(12) United States Patent
Peddinti et al.

(10) Patent No.: US 10,816,443 B2
(45) Date of Patent: Oct. 27, 2020

(54) AUTOMATED BATCH STAINER FOR IMMUNOHISTOCHEMISTRY

(71) Applicants:Kamal Prasad Peddinti, Hyderabad (IN); Neeraj Kumar, Fishers, IN (US)

(72) Inventors: Kamal Prasad Peddinti, Hyderabad (IN); Neeraj Kumar, Fishers, IN (US)

( * ) Notice: Subject to any disclaimer, the term of this patent is extended or adjusted under 35 U.S.C. 154(b) by 150 days.

(21) Appl. No.: 15/520,399

(22) PCT Filed: Oct. 19, 2015

(86) PCT No.: PCT/US2015/056274
§ 371 (c)(1),
(2) Date: Apr. 19, 2017

(87) PCT Pub. No.: WO2016/064760
PCT Pub. Date: Apr. 28, 2016

(65) Prior Publication Data
US 2017/0328821 A1 Nov. 16, 2017

Related U.S. Application Data

(60) Provisional application No. 62/065,734, filed on Oct. 19, 2014.

(51) Int. Cl.
*G01N 1/31* (2006.01)
*G01N 35/00* (2006.01)
(Continued)

(52) U.S. Cl.
CPC ............ *G01N 1/312* (2013.01); *G01N 33/52* (2013.01); *G01N 33/543* (2013.01);
(Continued)

(58) Field of Classification Search
CPC .... G01N 1/31; G01N 1/312; G01N 35/00029; G01N 35/0099; G01N 35/0092
See application file for complete search history.

(56) References Cited

U.S. PATENT DOCUMENTS 6,520,726 B1 * 2/2003 Cook ................ H01L 21/67766
414/217
9,945,763 B1 * 4/2018 Tacha ...................... G01N 1/312
(Continued)

FOREIGN PATENT DOCUMENTS

EP 0323130 A2 7/1989
EP 2533049 A1 12/2012
WO WO 2014/001530 1/2014

OTHER PUBLICATIONS

International Search Report and Written Opinion for PCT/US2015/056274, dated Jan. 28, 2016.
(Continued)

*Primary Examiner* — Christopher Adam Hixson
(74) *Attorney, Agent, or Firm* — Bryan D. Zerhusen, Esq.; Nicholas R. Herrel, Esq.; Cantor Colburn LLP

(57) ABSTRACT

An automated batch stainer for staining biological specimens on microscope slides. The automated batch stainer includes a slide rack assembly configured to hold microscope slides, a robotic arm that manipulates the slide rack assembly, at least one bath containing reagents and capable of receiving the slide rack assemblies, a heating chamber capable of heating multiple slide rack assemblies, a bar code reader, at least one software program including a graphical user interface and configured to calculate the timing and sequence of the staining protocol and implement the staining protocol by controlling the movements of the robotic arm.

19 Claims, 38 Drawing Sheets

(51) Int. Cl.
   *G01N 33/52* (2006.01)
   *G01N 33/543* (2006.01)
(52) U.S. Cl.
   CPC ... *G01N 35/00029* (2013.01); *G01N 35/0092* (2013.01); *G01N 35/0099* (2013.01); *G01N 2035/00039* (2013.01); *G01N 2035/0091* (2013.01); *G01N 2035/00138* (2013.01); *G01N 2035/00752* (2013.01); *G01N 2035/00831* (2013.01)

(56) References Cited

U.S. PATENT DOCUMENTS

| | | | |
|---|---|---|---|
| 2006/0178776 A1* | 8/2006 | Feingold | G01N 35/0092 700/245 |
| 2008/0089808 A1* | 4/2008 | Shah | G01N 1/312 422/65 |
| 2010/0191382 A1 | 7/2010 | Samuhel et al. | |
| 2011/0136135 A1 | 6/2011 | Larsen et al. | |
| 2011/0174088 A1 | 7/2011 | Watkins et al. | |
| 2013/0029409 A1 | 1/2013 | Sweet et al. | |
| 2014/0273088 A1* | 9/2014 | Winther | G01N 1/312 435/40.52 |
| 2014/0329270 A1* | 11/2014 | Favaloro | G01N 1/312 435/30 |

OTHER PUBLICATIONS

Supplementary European Search Report for EP 15851897.7, dated Jun. 6, 2018.

\* cited by examiner

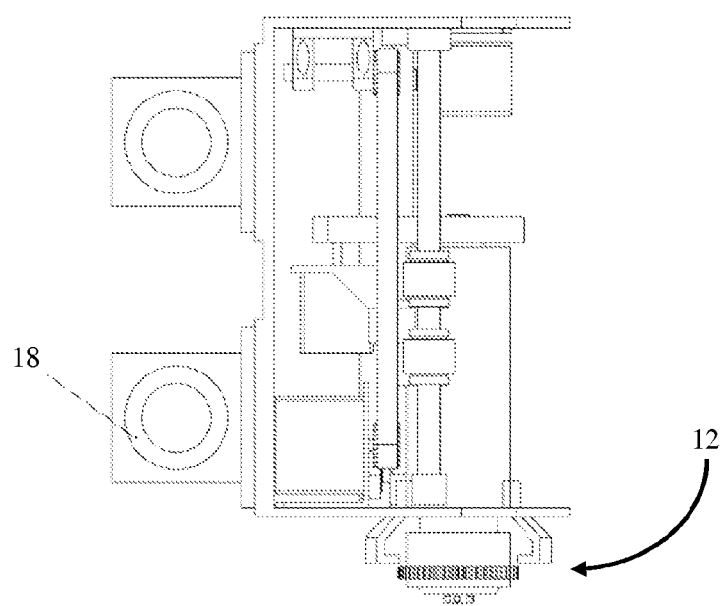

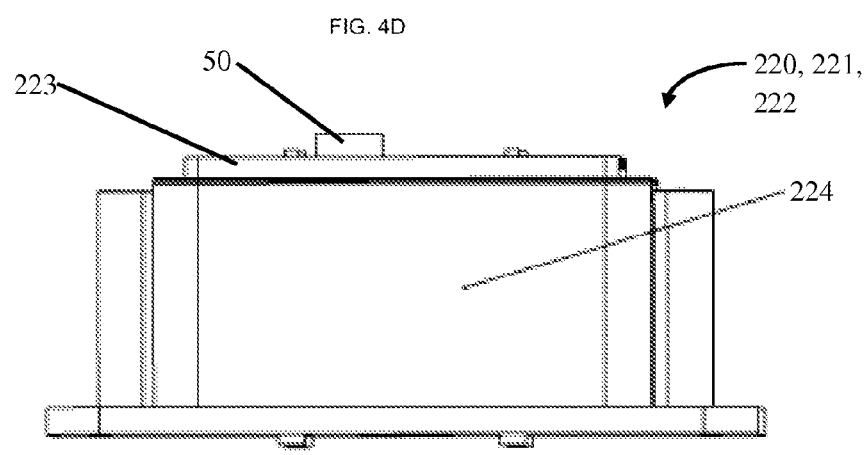
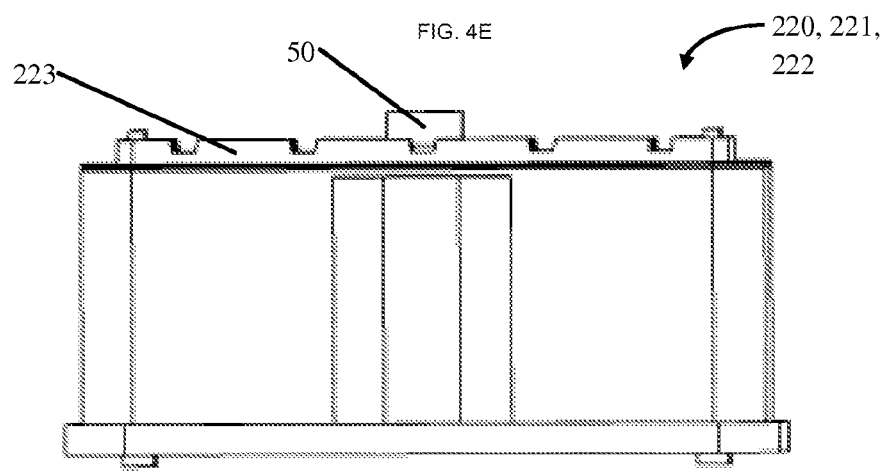

Slide Processing Schedule on Machine

|  | 1 | 2 | 3 | 4 | 5 | 6 | 7 | 8 | 9 | 10 |
|---|---|---|---|---|---|---|---|---|---|---|
|  | A | B | C | D | E | F | G | H | I | J |
|  | 0 | 10 | 610 | 620 | 1220 | 1230 | 1830 | 1840 | 2440 | 2450 |
|  | 0 | 0 | 0 | 0 | 0 | 0 | 0 | 0 | 0 | 0 |
| R A | 10 | 10 | 10 | 10 | 10 | 10 | 10 | 10 | 10 | 10 |
| Secondary 1 | 300 | 300 | 300 | 300 | 300 | 300 | 300 | 300 | 300 | 300 |
| R A | 10 | 10 | 10 | 10 | 10 | 10 | 10 | 10 | 10 | 10 |
| Rack Up Down | 10 | 10 | 10 | 10 | 10 | 10 | 10 | 10 | 10 | 10 |
| Secondary 1 | 300 | 300 | 300 | 300 | 300 | 300 | 300 | 300 | 300 | 300 |
| RA | 10 | 10 | 10 | 10 | 10 | 10 | 10 | 10 | 10 | 10 |
| Wash 1 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Wash 2 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Wash 3 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Primary | 600 | 600 | 600 | 600 | 600 | 600 | 600 | 600 | 600 | 600 |
| R A | 10 | 10 | 10 | 10 | 10 | 10 | 10 | 10 | 10 | 10 |
| Rack Up Down | 10 | 10 | 10 | 10 | 10 | 10 | 10 | 10 | 10 | 10 |
| Primary | 600 | 600 | 600 | 600 | 600 | 600 | 600 | 600 | 600 | 600 |
| R A | 10 | 10 | 10 | 10 | 10 | 10 | 10 | 10 | 10 | 10 |
| Rack Up Down | 10 | 10 | 10 | 10 | 10 | 10 | 10 | 10 | 10 | 10 |
| Primary | 600 | 600 | 600 | 600 | 600 | 600 | 600 | 600 | 600 | 600 |
| RA | 10 | 10 | 10 | 10 | 10 | 10 | 10 | 10 | 10 | 10 |
| Wash 1 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Wash 2 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Wash 3 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Secondary 2 | 300 | 300 | 300 | 300 | 300 | 300 | 300 | 300 | 300 | 300 |
| R A | 10 | 10 | 10 | 10 | 10 | 10 | 10 | 10 | 10 | 10 |
| Rack Up Down | 10 | 10 | 10 | 10 | 10 | 10 | 10 | 10 | 10 | 10 |
| Secondary 2 | 300 | 300 | 300 | 300 | 300 | 300 | 300 | 300 | 300 | 300 |
| R A | 10 | 10 | 10 | 10 | 10 | 10 | 10 | 10 | 10 | 10 |
| Wash 1 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Wash 2 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Wash 3 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Secondary 3 | 300 | 300 | 300 | 300 | 300 | 300 | 300 | 300 | 300 | 300 |
| R A | 10 | 10 | 10 | 10 | 10 | 10 | 10 | 10 | 10 | 10 |
| Rack Up Down | 10 | 10 | 10 | 10 | 10 | 10 | 10 | 10 | 10 | 10 |
| Secondary 3 | 300 | 300 | 300 | 300 | 300 | 300 | 300 | 300 | 300 | 300 |
| R A | 10 | 10 | 10 | 10 | 10 | 10 | 10 | 10 | 10 | 10 |
| Wash 1 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Wash 2 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Wash 3 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Secondary 4 | 300 | 300 | 300 | 300 | 300 | 300 | 300 | 300 | 300 | 300 |
| R A | 10 | 10 | 10 | 10 | 10 | 10 | 10 | 10 | 10 | 10 |
| Wash 1 | 60 | 60 | 60 | 60 | 60 | 60 | 60 | 60 | 60 | 60 |

| | | | | | | | | | | |
|---|---|---|---|---|---|---|---|---|---|---|
| R A | 10 | 10 | 10 | 10 | 10 | 10 | 10 | 10 | 10 | 10 |
| Wash 2 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Wash 3 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Secondary 5 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Wash 1 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Wash 2 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Wash 3 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Wash D1 | 60 | 60 | 60 | 60 | 60 | 60 | 60 | 60 | 60 | 60 |
| R A | 10 | 10 | 10 | 10 | 10 | 10 | 10 | 10 | 10 | 10 |
| Park | | | | | | | | | | |
| | 5460 | 5470 | 6070 | 6080 | 6680 | 6690 | 7290 | 7300 | 7900 | 7910 |
| | A | B | C | D | E | F | G | H | I | J |
| Time for each Rack in mins. | 91.00 | 91.17 | 101.17 | 101.33 | 111.33 | 111.50 | 121.50 | 121.67 | 131.67 | 131.8333 |

Times (secs) for Cooker loading, unloading & starting during run.

AUTOMATED BATCH STAINER FOR IMMUNOHISTOCHEMISTRY

CROSS-REFERENCE TO RELATED APPLICATIONS

This application is a National Stage of PCT/US2015/056274, filed 19 Oct. 2015, titled AUTOMATED BATCH STAINER FOR IMMUNOHISTOCHEMISTRY and which claims the benefit of U.S. Provisional Application Ser. No. 62/065,734, filed 19 Oct. 2014, both of which are incorporated by referenced herein in their entireties for all purposes.

BACKGROUND OF THE INVENTION

The present invention relates generally to automated immunohistochemistry stainers and more specifically it relates to an automated batch stainer for immunohistochemistry for staining of biological specimens on microscope slides.

Other immunohistochemistry stainers developed for manipulating slides and reagent to stain slides by immunohistochemistry have a robot that can add or remove processing fluids to microscope slides. These strainers, however, deliver a small amount of processing fluid onto a microscope slide that is oriented in a horizontal position, such that the processing fluid would contact the biological sample. As a result, each slide within a run would be treated sequentially with a processing fluid. That is, after a first slide was processed, the robot moves to the next slide in the sequence, and this sequential processing would continue through each slide until all slides within the run had been processed. The type of slide processing that is performed by these instruments could be described as sequential processing as each slide is individually treated in a sequential manner.

BRIEF SUMMARY OF THE INVENTION

The invention generally relates to an automated stainer, for example automated immunohistochemistry staining, that includes a slide rack assembly, a mechanical robotic arm that manipulates the slide rack assemblies, multiple baths containing processing fluids and capable of receiving the slide rack assemblies, a heating chamber capable of heating at least one slide rack assembly, at least one software program containing a graphical user interface (GUI) and calculates the timing sequence for the staining protocol and the robotic arm movements for the staining protocol. In an embodiment, the automated stainer includes a bar code reader. The baths can include reagent containers with primary antibodies, detection reagents, antigen retrieval solution/agent, wash buffer, water, etc., which include processing fluids, such as a primary antibody or antibodies, detection reagents (e.g., secondary antibody with a conjugated enzyme, and chromogen), antigen retrieval solution/agent, wash buffer, water (e.g., deionized water), or other processing fluids known by one skilled in the art. In some embodiments, the automated stainer includes multiple sets of detection systems (e.g., secondary antibody with enzyme, substrate and counterstain). Furthermore, multiple slide racks can be processed in parallel. In a certain embodiment, the automated stainer can perform batch and a continuous run in the same run. In a particular embodiment, the processing fluids are utilized for 50 to 70 slides before being replaced.

In this respect, before explaining at least one embodiment of the disclosure in detail, it is to be understood that the embodiments of the disclosure are not limited in its application to the details of construction or to the arrangements of the components set forth in the following description or illustrated in the drawings. One skilled in the art would appreciate that the present disclosure is capable of other embodiments and of being practiced and carried out in various ways. Also, it is to be understood that the phraseology and terminology employed herein are for the purpose of the description and should not be regarded as limiting.

An object of the disclosure is an automated stainer for specimens on microscope slides. For example, the specimens include cell smears, frozen and paraffin embedded specimens including biological specimens. In an embodiment, the automated stainer performs staining in a batchwise manner. For example, a batch of microscope slides may be placed in a slide rack assembly, multiple of which can be incubated in the same processing fluid. The automated stainer can perform, for example, immunohistochemistry staining and/or post in situ hybridization staining.

Another object of the disclosure is an automated stainer that stains biological samples on microscope slides by adding and removing processing fluids (reagents) simultaneously from a set of microscope slides contained in a slide rack assembly.

Another object of the disclosure is an automated batch stainer that manipulates multiple slide rack assemblies comprising multiple microscope slides by immersing the slide rack assemblies into a series of tanks comprising processing fluids. In an embodiment, after a first slide rack assembly has completed its incubation in a first processing fluid, it is removed and transferred to a second processing fluid, while a second slide rack is immersed into the first processing fluid. In certain embodiments, the automated batch stainer performs immunohistochemistry staining and/or in situ hybridization.

Another object of the disclosure is an automated batch stainer comprising a robotic arm that sequentially moves multiple slides rack assemblies through multiple processing fluids. Each slide rack assembly is sequentially moved through a series of processing fluids after the preceding slide rack assembly has completed its incubation and moved to the next processing fluid. In certain embodiments, the automated batch stainer performs immunohistochemistry staining and/or in situ hybridization.

Another object of the present disclosure is an automated batch stainer with a robotic arm that treats each slide rack assembly sequentially through a series of processing fluids, wherein each microscope slide contained within the slide rack assembly is treated simultaneously to the processing fluid in which the slide rack assembly is immersed. In certain embodiments, the automated batch stainer performs immunohistochemistry staining and/or in situ hybridization.

Another object of the disclosure is an automated batch stainer that is controlled by a software program that calculates the timing of the movement of the slide rack assemblies through the processing fluids, schedules the time of each movement, and signals the robotic arm to move the slide racks at the scheduled times.

Another object of the present disclosure is an automated batch stainer comprising a heating chamber capable of holding multiple slides racks, said chamber is capable of being pressurized and maintaining an internal temperature greater than 100° C.

Another object of the present disclosure is an automated batch stainer comprising a heated chamber capable of performing antigen retrieval on specimens on the single to multiple microscope slides in bulk processing.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIGS. 1A, 1B, 1C, 1D, 1E, and 1F: FIG. 1A-1F illustrate a mechanical robotic arm 10 of the present disclosure. The articulated robot 10 is constructed from a series of interconnected joints. Its biggest advantage is flexibility and ability to approach a given x, y, z point with any desired yaw, pitch, and roll (within the robot's mechanical limitations).

FIGS. 2A, 2B, 2C, 2D, 2E, 2F, 2G, 2H, and 2I: FIGS. 2A-2I illustrate a slide rack assembly according an embodiment of the present disclosure. The slide rack assembly holds multiple slides in a vertical orientation. The slide rack lid 52 is shown in the closed and open position. In the open position, slides can be inserted or removed from the slide rack body 51. In a close position, the slides are secured within the slide rack body 51.

FIGS. 3A-3C illustrate a stainer 200 according to an embodiment of the present disclosure.

FIGS. 4A, 4B, 4C, 4D, 4E, and 4F: FIGS. 4A-4F illustrate a holding rack 220, 221, 222 according to an embodiment of the present disclosure.

FIGS. 5A-5E illustrate a reagent container rack 230, 231 according to the present disclosure. The reagent container rack includes reagent containers 232 that contain a reagent. When the slide rack assembly (and its associated slides) are placed into the reagent container 232, the slides become submerged in the reagent. The reagent containers 232 are shown with an open reagent container lid 233 for inserting or removing the slide rack assemblies.

FIGS. 6A and 6B illustrate a reagent container 232 and reagent container lid 233 according to an embodiment of the present disclosure. As depicted, the slide rack assemble has been at least partially inserted into the reagent container 232.

FIGS. 7A-7F illustrate a buffer wash tank assembly 240 according to an embodiment of the present disclosure. As depicted, the buffer wash tank includes three buffer wash tanks 241, each of which includes two positions for a slide rack assembly 50 to be inserted.

FIG. 8 is a heating chamber 250, 251 according to an embodiment of the present disclosure, which as depicted includes a heating vessel 250 and a heating vessel lid 251. The heating chamber is composed of a cylindrical container with a lid. The interior of the chamber contains a small amount of water which generates steam during the heating process to increase the internal pressure. The heating chamber also contains reagent baths that can accept slide racks for performing antigen retrieval on the associated slides.

FIGS. 9A and 9B illustrate a water wash tank assembly 260 according to an embodiment of the present disclosure. As depicted, the water wash tank assembly 260 includes two water wash tanks 261, each of which includes two positions for a slide rack assembly 50 to be inserted.

FIGS. 10A and 10B illustrate another layout for the platform 211 of the stainer 200 with FIG. 10B includes the robotic arm 10.

FIG. 11: FIG. 11 shows a run sequence and timing of events for a particular Scheduler run according to an embodiment of the present disclosure. The Scheduler controls the movement of the slide rack assemblies through the processing fluids.

FIG. 12A shows another slide processing schedule of the stainer according to an embodiment of the present disclosure. FIG. 12B graphically illustrates the timing of each slide rack assembly of FIG. 12A as it proceeded through the stainer.

DETAILED DESCRIPTION OF THE INVENTION

Figure 1A:
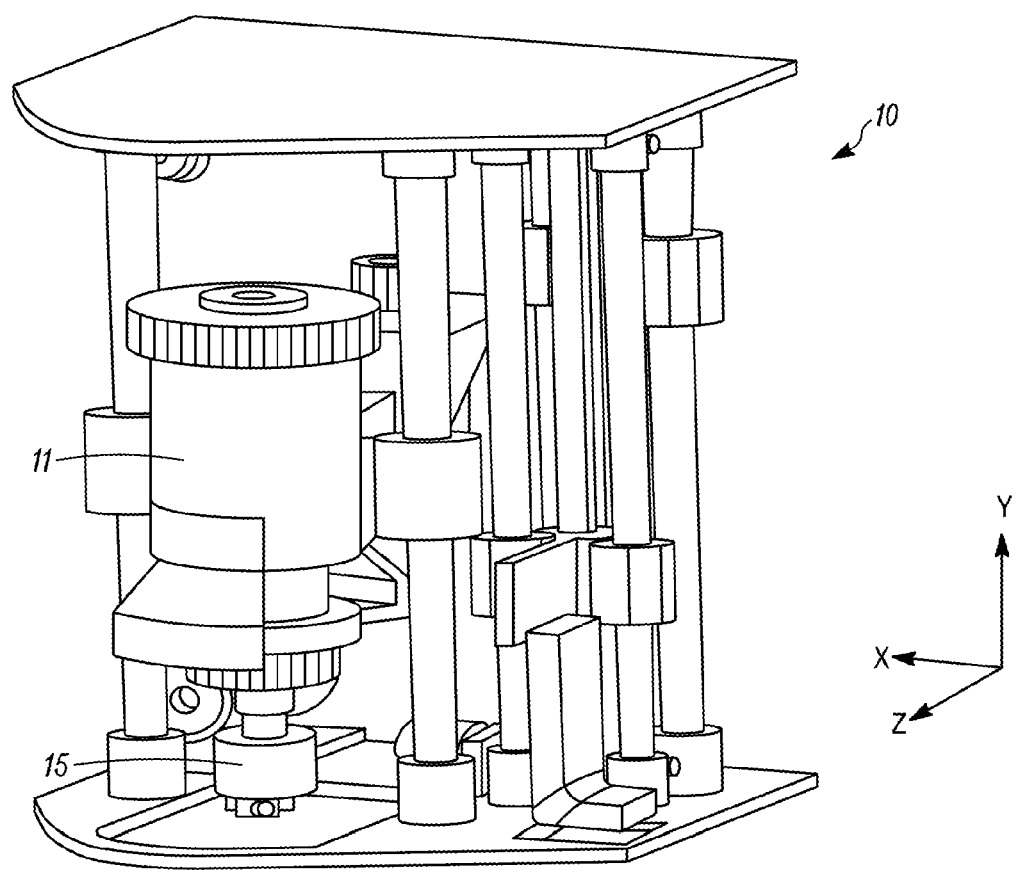

The following is a detailed description of the disclosure provided to aid those skilled in the art in practicing the present disclosure. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description of the disclosure herein is for describing particular embodiments only and is not intended to be limiting of the disclosure. All publications, patent applications, patents, figures and other references mentioned herein are expressly incorporated by reference in their entirety.

The drawings, in which similar reference characters denote similar elements throughout the several views, illustrate a slide rack, a mechanical device comprised of a robotic arm that manipulates slide rack assemblies, baths containing reagents and capable of receiving the slide rack assemblies, a heating chamber capable of heating multiple slide rack assemblies and slides, a bar code reader, a software program containing a graphical user interface (GUI), a software program for controlling the robot movements, and a software program for calculating the timing sequence for each movement.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the 10 United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

Mechanical Robotic Arm

FIGS. 1A through 1F illustrate a mechanical robotic arm 10. In an embodiment, the robotic arm 10 includes a grip assembly 11 attached to a mechanical robotic head 12. The robotic arm 10 can move the robotic head 12 three dimensionally, e.g., x, y and z directions.

Figure 1B:
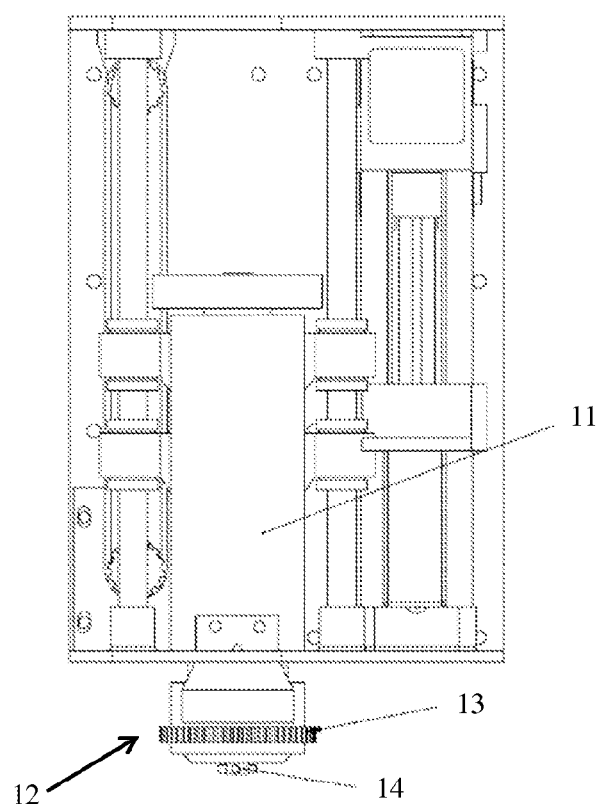
Figure 1C:
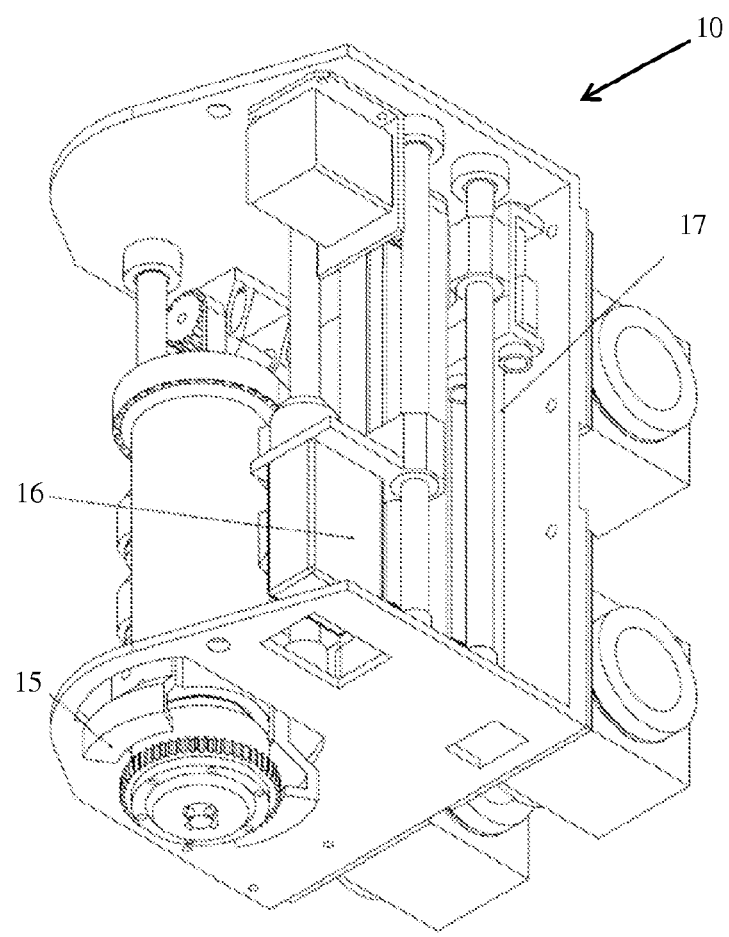

FIG. 1B illustrates an embodiment of the robotic head 12. In an embodiment, the robotic head 12 includes a rotation gear 13. In another embodiment, the robotic head 12 includes a slide interfacing assembly 14. As illustrated in FIG. 1C, robotic head 12 can include a rotation lock 15. Furthermore, the robotic arm 10 can include a bar code reader 16 and/or a liquid handling assembly 17. The liquid handling assembly 17 dispenses processing fluids, e.g. buffers including antigen retrieval and wash buffers, as well as water. Furthermore, the liquid handling assembly 17 can also aspirate processing fluids, e.g. buffers and water. The robotic arm includes 10 linear motion bearing(s) 18. See, for example, FIG. 1D.

In an embodiment, the robotic head 12 is configured to engage with at least one of: a slide rack assembly 50, a slide rack lids 51, and a heating chamber 250, 251. That is, in certain embodiments, the movement of the robotic arm 10 is configured to open and close lids located on the processing fluids. For example, the rotation gear can lock and unlock the heating chamber 250, 251. In certain embodiments there can be more than one lid per reagent bath and/or more than one reagent bath that the robotic arm 10 is configured to open and close, for example there can be one, two, three, four or more lids per reagent bath, and there can be one, two, three, four, five, six, or more reagent baths. In an embodiment, the robotic arm 10 is configured to open and close a heating vessel lid 251. The robotic arm 10 is configured to move the slide racks 50 and associated microscope slides 51 to the various processing fluids.

Figure 1E:
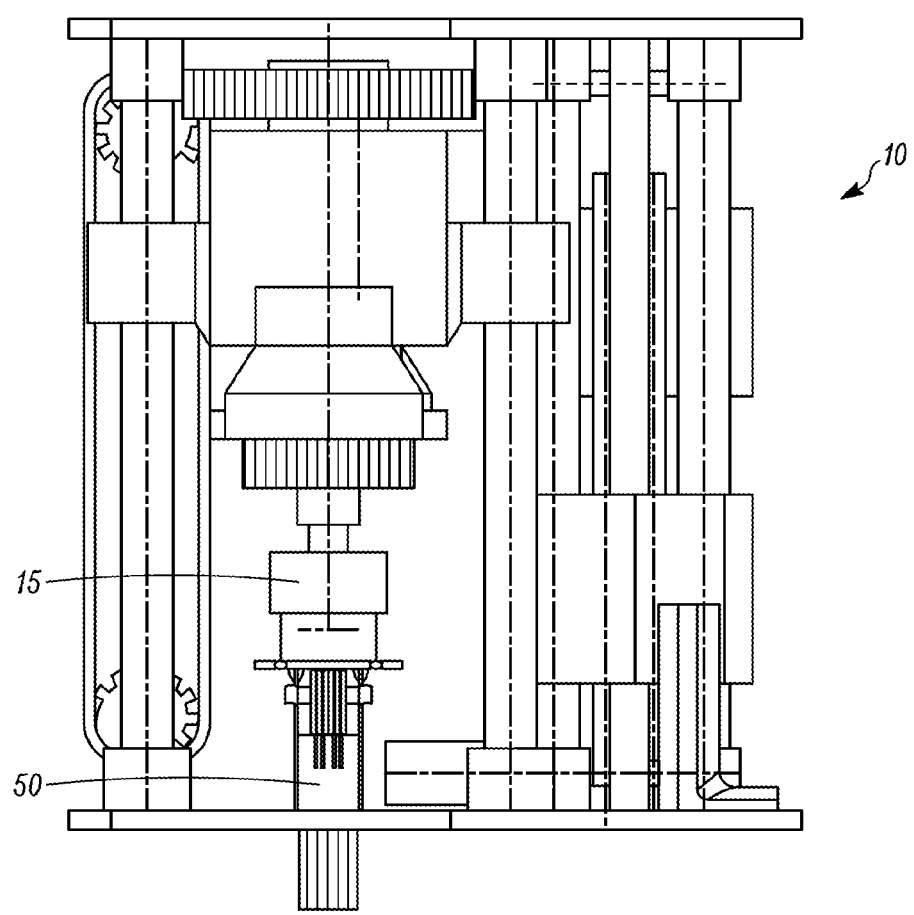
Figure 1F:
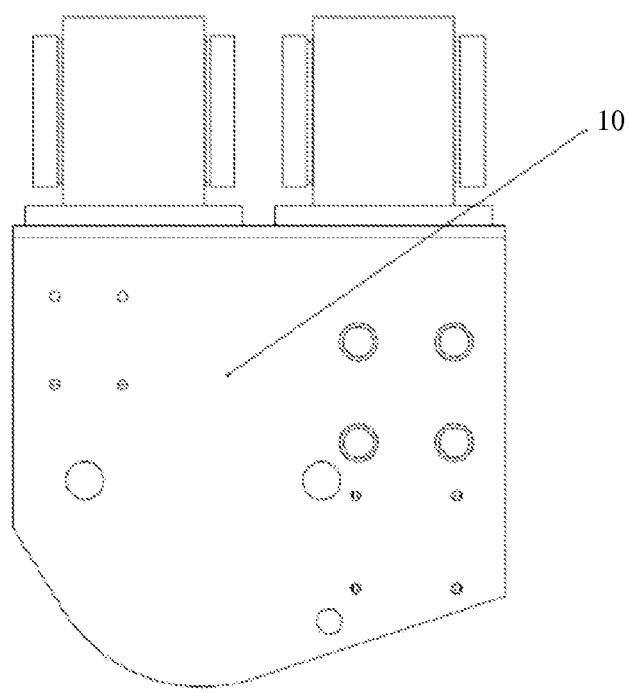

FIG. 1E illustrates the robotic head 12 as it engages with the slide rack 50 to move the slide rack through a series of processing fluid baths. One skilled in the art would appreciate that the slide interface assembly can engage by many different mechanisms. FIG. 1F illustrates top view of the robotic arm 10.

The robotic arm could contain various different types of engagement designs as long as the robot arm could still engage with the lids and slide racks as described throughout the specification. Furthermore, the robotic arm could move in a radial direction around a circular center, rather than a traditional x, y, and z motion.

Slide Rack

FIGS. 2A, 2B, 2F, 2G, and 2H illustrates an embodiment of a slide rack assembly 50, which holds up to 5 microscope slides 100. Alternatively, the slide rack assembly 50 can hold more or fewer microscope slides 100 depending upon the performed staining procedure. For example, the slide rack assembly 50 can hold 1, 2, 3, 4, 5, 6, 7, 8, 9, 10, 11, 12, 13, 14, 15, 16, 17, 18, 19, 20, 21, 22, 23, 24, 25, or more microscope slides 100. Furthermore, the slide rack assembly 50 is configured to engage with the robotic arm 10, such that the robotic arm 10 can move the slide rack sequentially through a series of processing fluid baths. For example, the slide rack assembly 50 to be acquired by and released from the robotic arm 10, for example through a slide interface assembly 14.

In an embodiment, the slide rack assembly comprises a slide rack body 51 and a slide rack lid 52. The slide rack lid 52 can be configured to secure the microscope slides 100 in the slide rack body 51. For example, when the slide rack lid 52 is open, the microscope slides 100 are inserted in a vertical orientation into a slide rack body 51, which comprising groves to keep each microscope slide 100 separated from the next slide, e.g. about 1.33 mm. Once the desired microscope slides have been inserted in the slide rack body 51, the slide rack lid 52 can be closed to secure the microscope slides within the slide rack body/assembly for processing. In an embodiment, the slide rack lid 52 includes a robotic arm interface or socket 53. The robotic arm interface or gripper 53 is designed such that the robotic arm 10 (e.g., through a slide interface assembly 14 of the robotic head 12) can releasably engage with the slide rack assembly 50. For example, the robotic arm 10 can acquire (i.e., pick up, grip, or attach) a slide rack assembly 50, move the slide rack assembly 50 to a new location, and release (i.e., let go or ungrip) the slide rack assembly 50 at the new location. Furthermore, the slide rack assembly 50 is designed to immerse the microscope slides 100 into fluids, which will be discussed in greater detail below. For example, the slide rack assembly 50 or the slide rack body 51 includes at least one slide rack opening 54 that allow fluids to enter the slide rack assembly 50 to contact the microscope slides 100 and samples thereon when submerged in a fluid.

FIG. 2C illustrates a slide rack body 51 according to an embodiment of the invention that includes at least one slide rack opening 54. Although dimensions are shown for the particular embodiment, one skilled in the art would appreciate that the dimensions depend upon the dimensions of the processing fluid baths.

Figure 2A:
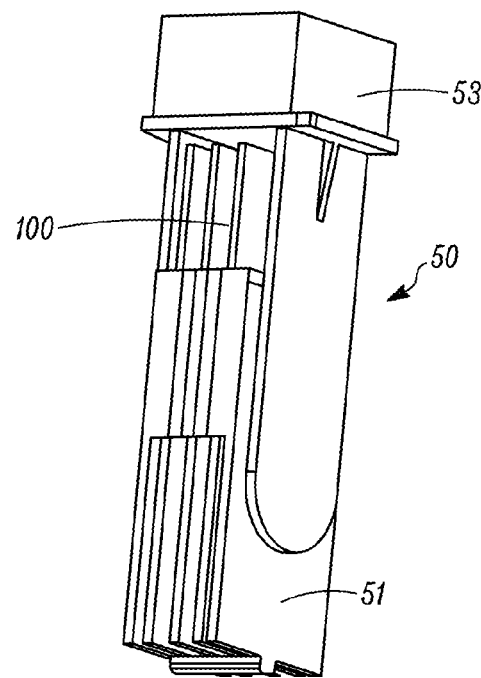
Figure 2B:
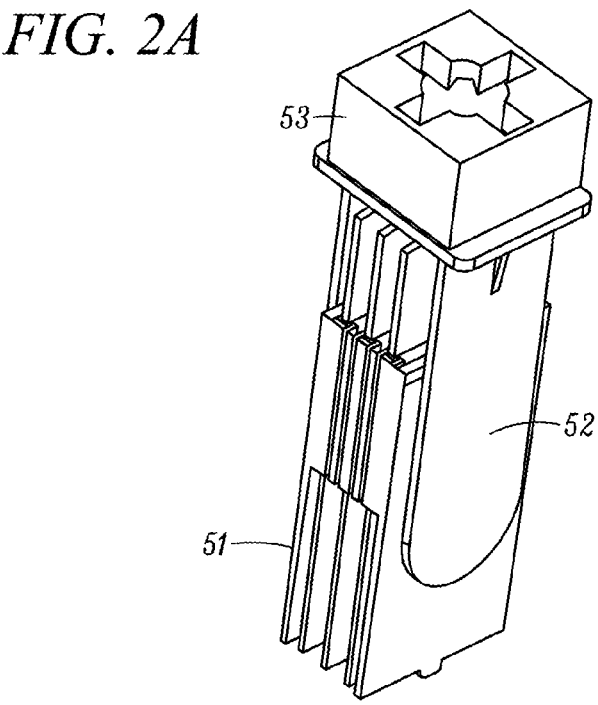
Figure 2E:
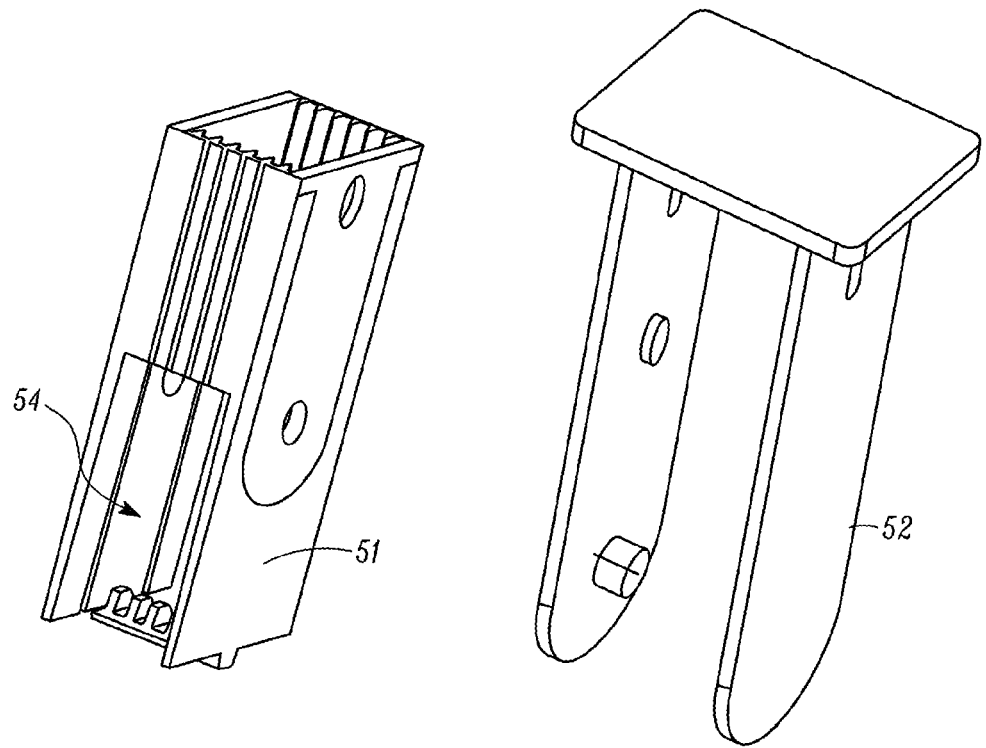
Figure 2E:
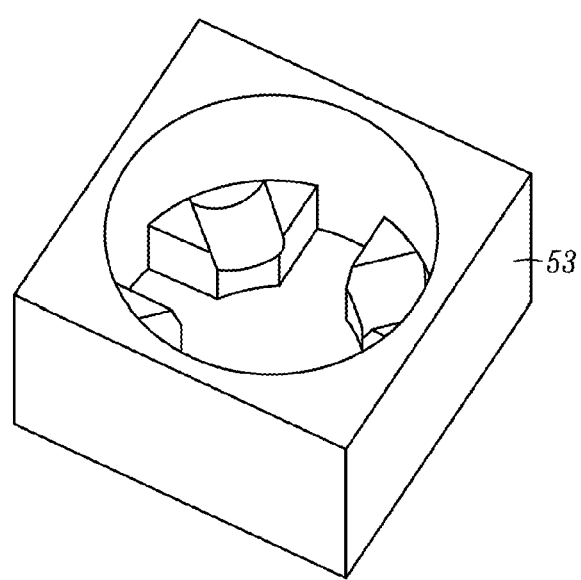
Figure 2F:
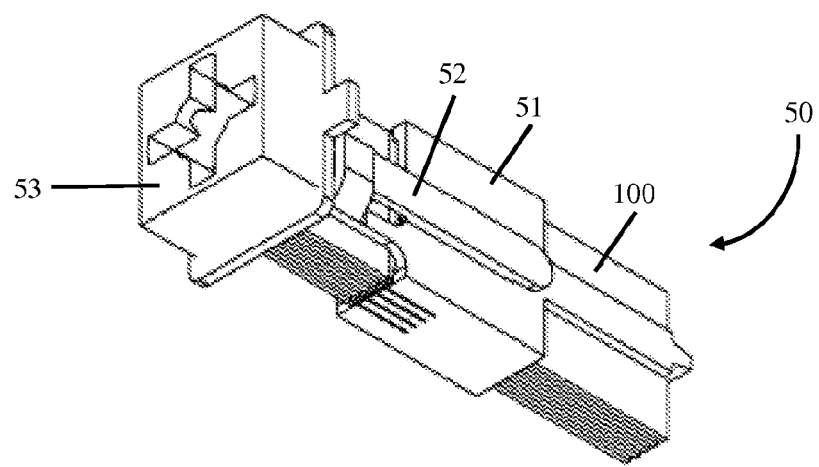
Figure 2G:
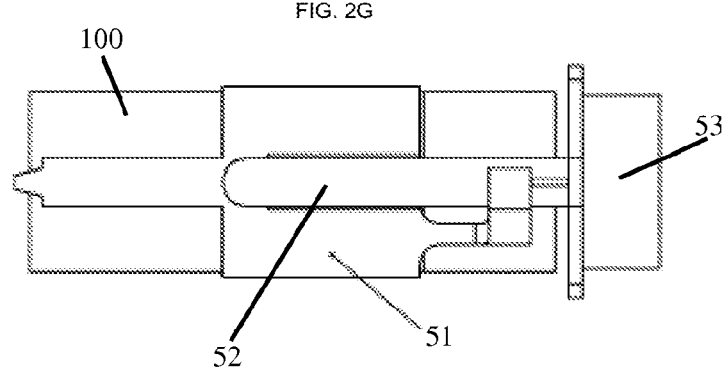
Figure 2H:
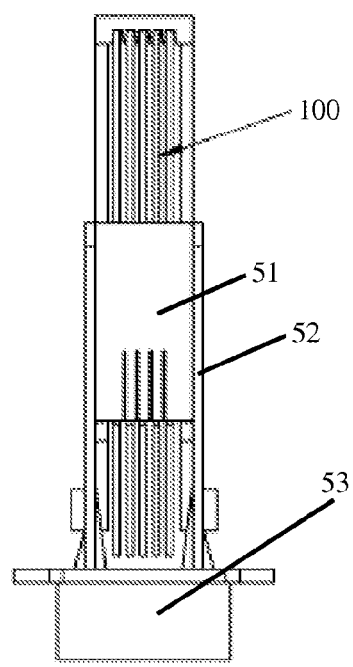
Figure 2I:
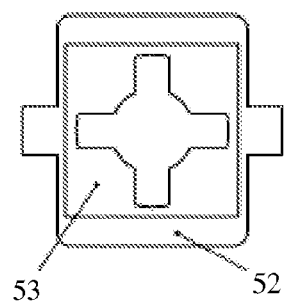

FIG. 2D illustrates the slide rack lid 52 without the robotic arm interface 53, which is shown inverted in FIG. 2E. The slide rack 52 lid and the robotic arm interface 53 can be a unitary molded piece or constructed of two or more pieces. In an embodiment, the robotic arm interface 53 includes a circular locking system. In certain embodiment, the circular locking system is locked to the robotic arm 10 by rotation. For example, in an embodiment, the slide interface assembly 14 is inserted into the robotic arm interface 53 and the interfaces are secured through relative rotation of the slide interface assembly 14 and the robotic arm interface 53. That is, in an embodiment, either the slide interface assembly, the robotic arm interface, or both, are rotated to lock/secure the slide rack assembly to the robotic arm 10. For example, FIG. 2E illustrates entry grooves 61 for the robotic arm 10 to grip the slide rack assembly 50 and locking grooves 62 for the robotic arm 10. Although FIG. 2E illustrates four entry grooves 61 and four locking grooves 62, one skilled in the art would appreciate that any mechanism capable of securing the slide rack assembly 50 and the robotic arm 10 can be utilized. For example, the slide rack assembly 50 can include 1, 2, 3, 4, 5, 6, 7, or 8 entry groves for the robotic arm 10 to secure the slide rack assembly 50. The slide rack assembly 50 can include 1, 2, 3, 4, 5, 6, 7, or 8 locking grooves for the robotic arm 10. FIG. 2I illustrate a top down view of the robotic arm interface 53 on the slide rack lid 52.

In an embodiment, the slide rack assembly 50 includes a bar code (not shown) that identifies the unique staining procedure for the microscope slides contained therein.

Other types of slide racks assemblies could be designed that provide a similar functions as long as the slide rack assemblies contain the same functional characteristics including, for example, holds multiples microscope slides, allows the slide rack assembly to be submerged into a fluid, and allows the microscope slides within the slide rack assembly to be exposed to the fluid it is submerged in.

Automated Stainer

Figure 3A:
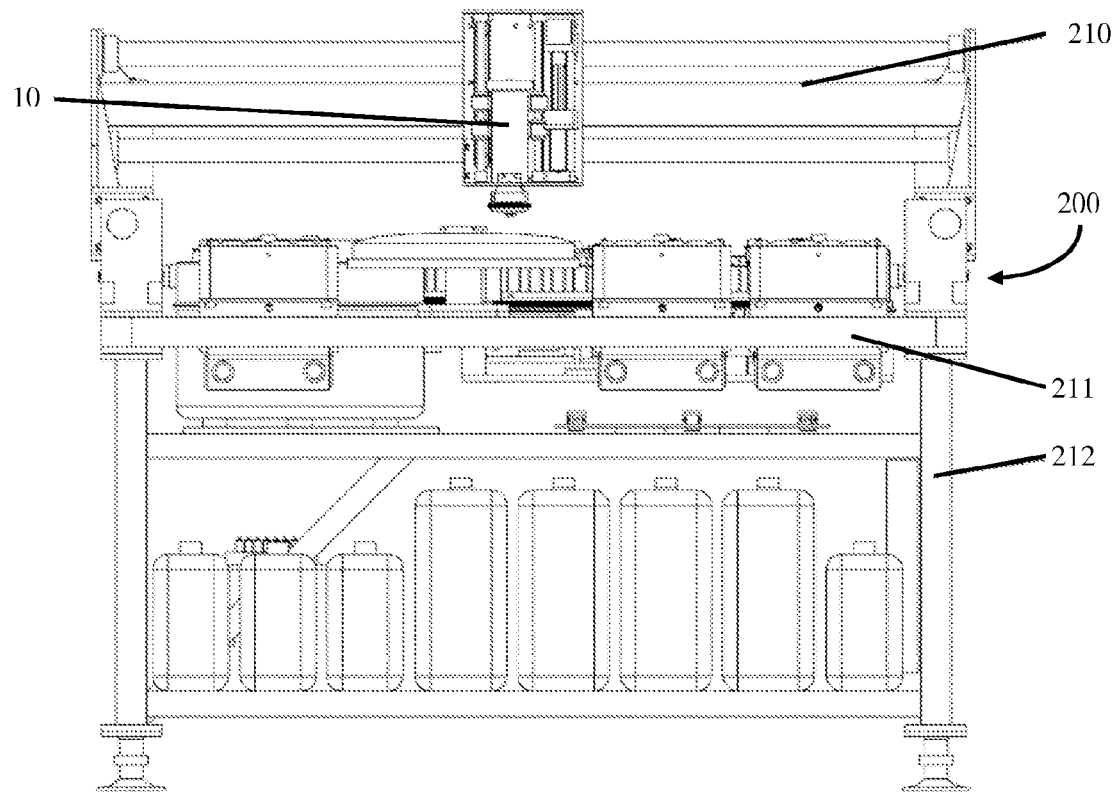
FIGS. 3A, 3B, and 3C.
Figure 3B:
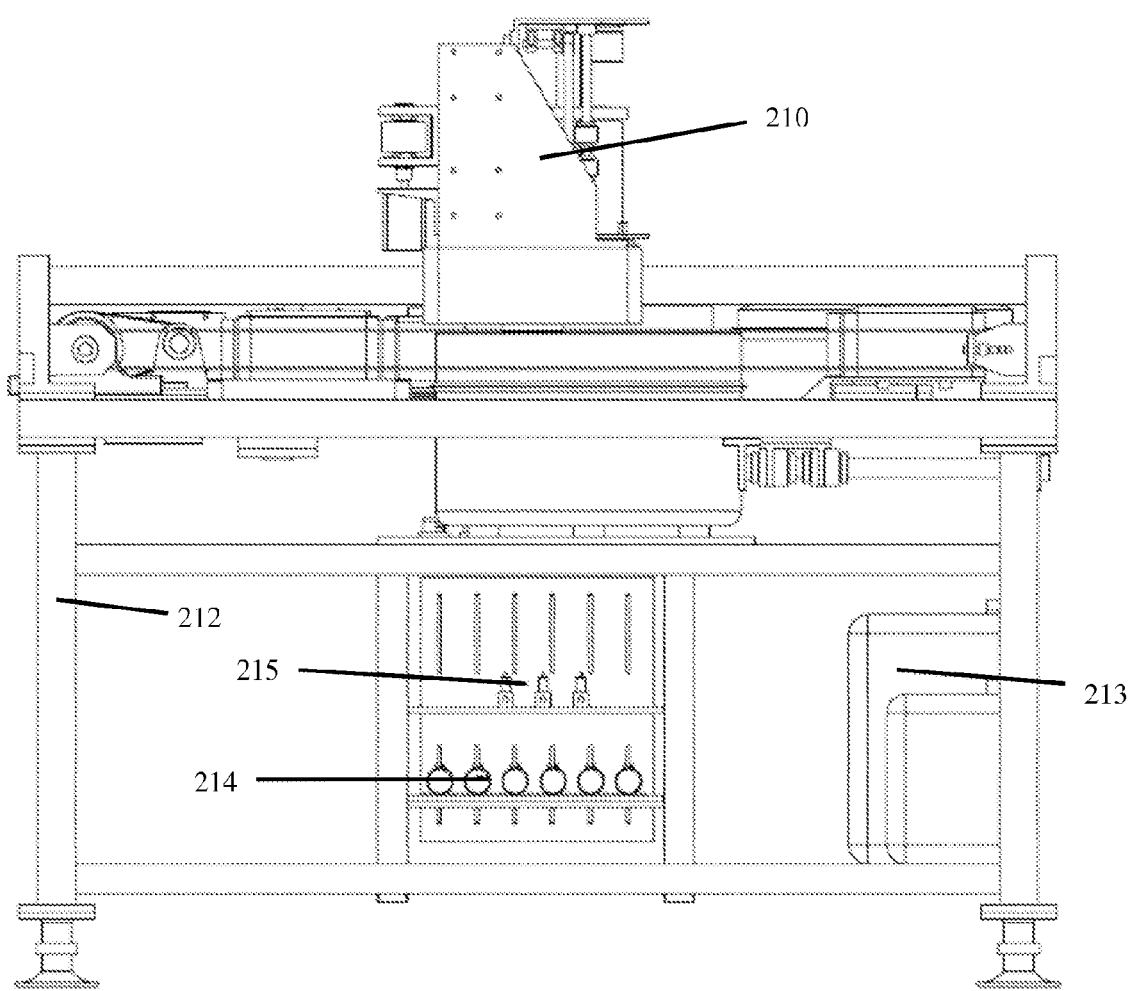
Figure 3C:
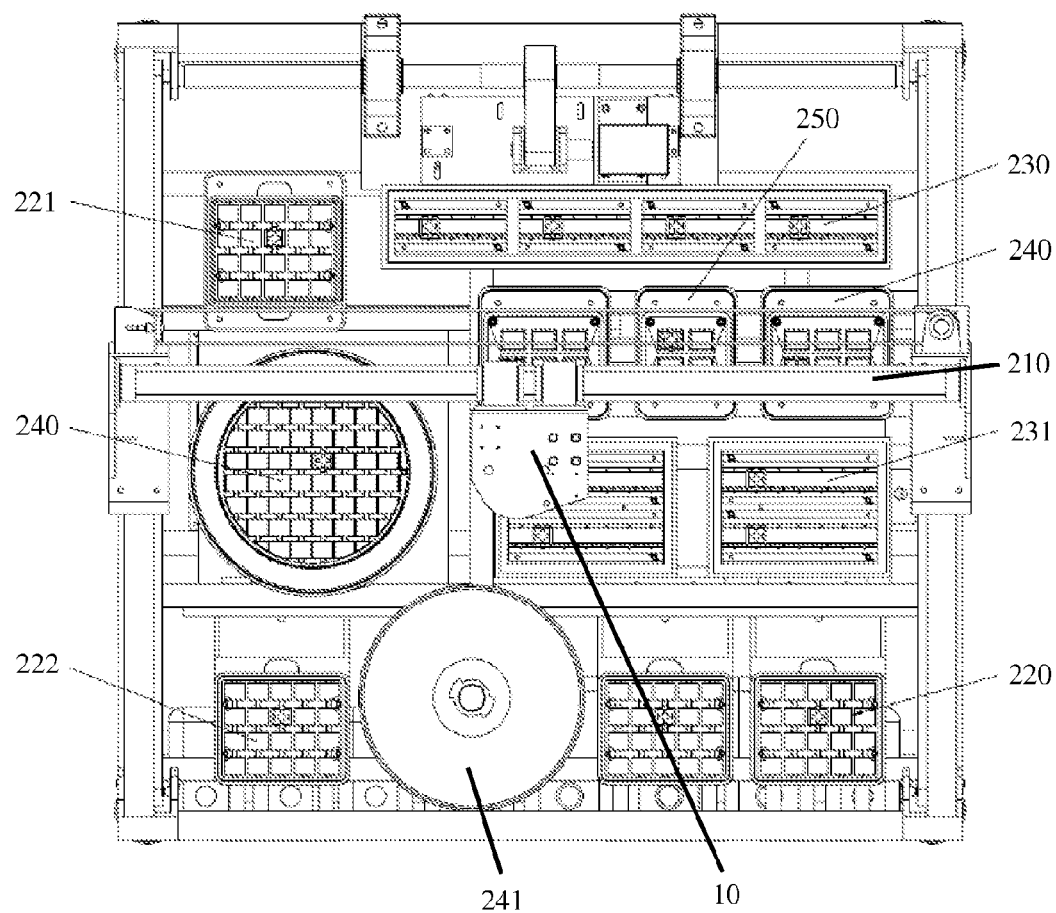

In an embodiment, as shown in FIGS. 3A-3C, a stainer 200 contains a mechanical robotic arm 10, a robotic arm gantry, 210 and a platform 211 that includes at least one processing fluid bath. The automated stainer 200 can be located on a stand 212. The stand can include at least one liquid container 213, at least one liquid pump 214, and at least one control valve 215. The at least one liquid container 213 can include processing fluids, e.g. antigen retrieval buffer(s), wash buffer(s), and water (such as deionized water). The at least one liquid container can be in fluid communication with the liquid handling assembly 17. In an alternative embodiment, the automated stainer 200 is located on a table, lab bench, or some other similarly situated surface. The processing fluid bath can include at least one of: (i) at least one holding rack 220, 221, 222; (ii) at least one reagent container rack 230, 231; (iii) at least one buffer wash tank assembly 240; (iv) at least one heating chamber 250, 251; and (v) at least one water wash tank assembly 260.

Figure 4A:
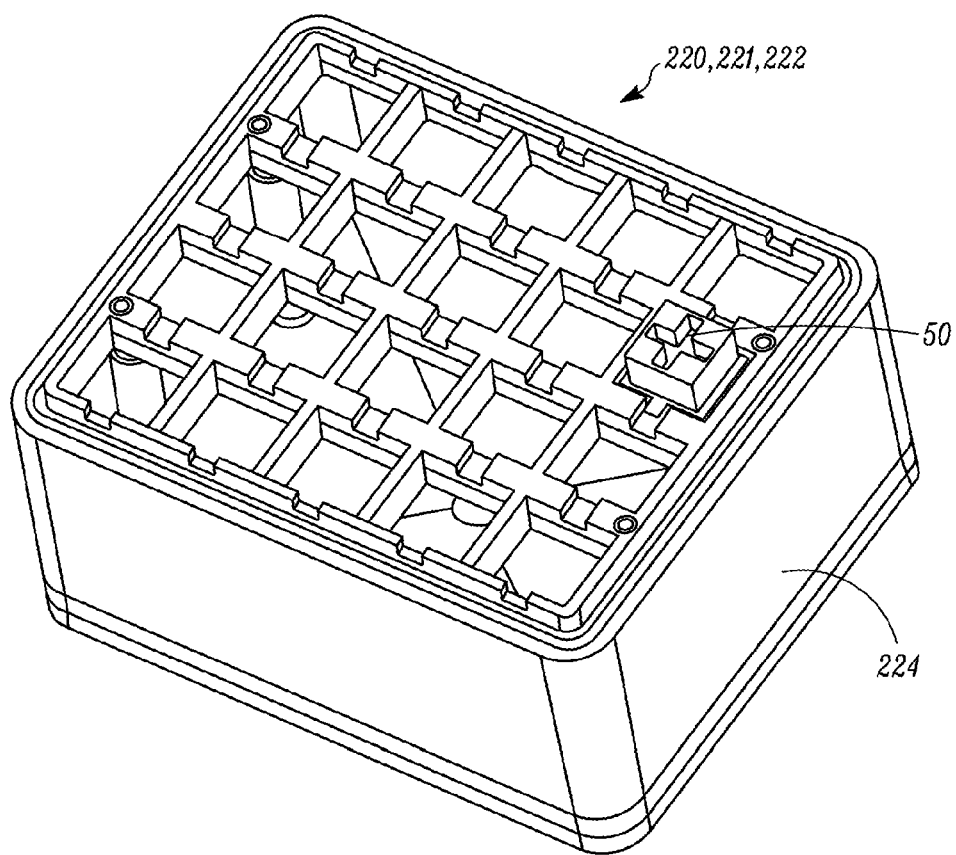
Figure 4B:
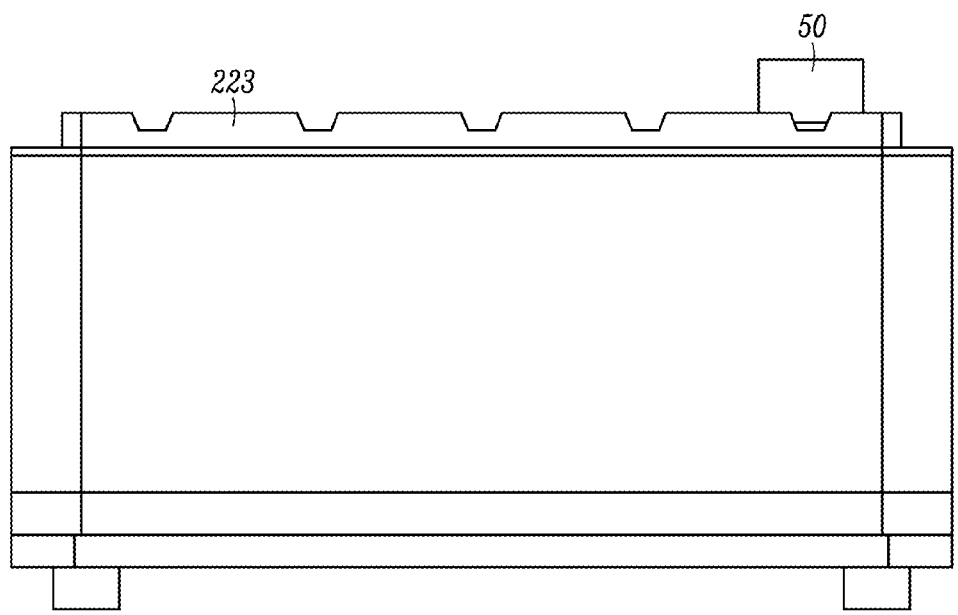
Figure 4C:
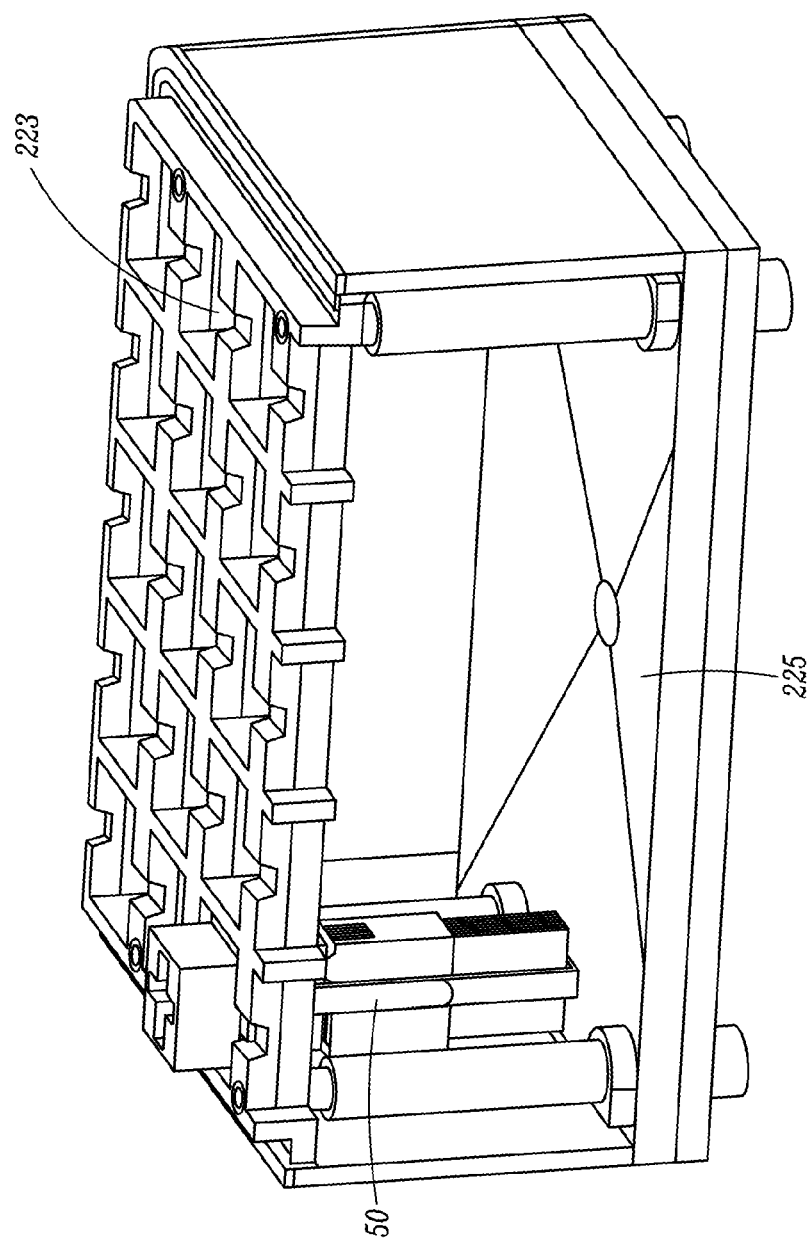
Figure 4F:
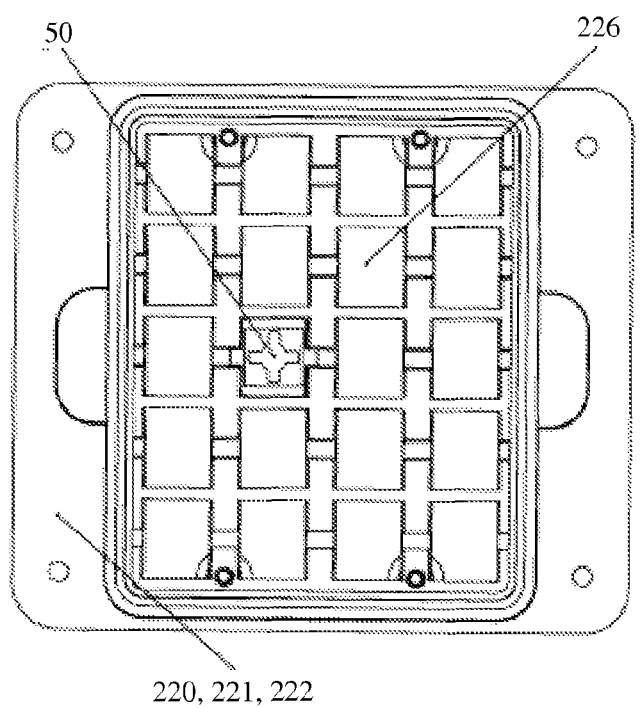

In an embodiment, the holding rack can be utilized for a slide rack assembly loading area, a slide rack assembly waiting area, and/or a slide rack assembly unloading area. For example, a holding rack 222 can be utilized for loading slide rack assemblies 50. The holding rack can also be utilized as a buffer waiting area 221 or as a rack unloading area 220 for slide rack assemblies 50. Furthermore, a single holding rack could be utilized for any combination of holding times, including, for example, a slide rack assembly loading area, a slide rack assembly waiting area, and a slide rack assembly unloading area. FIGS. 4A, 4B, and 4C illustrate an embodiment of the holding rack 220, 221, 222. The holding rack includes a slide rack holding assembly 223 with at least one slide rack assembly loading position 226, i.e. a position configured to receive a slide rack assembly 50, and a tapered bottom 224 that allows for any liquid in the holding rack 220, 221, 222 to be drained via a hole.

Figure 5A:
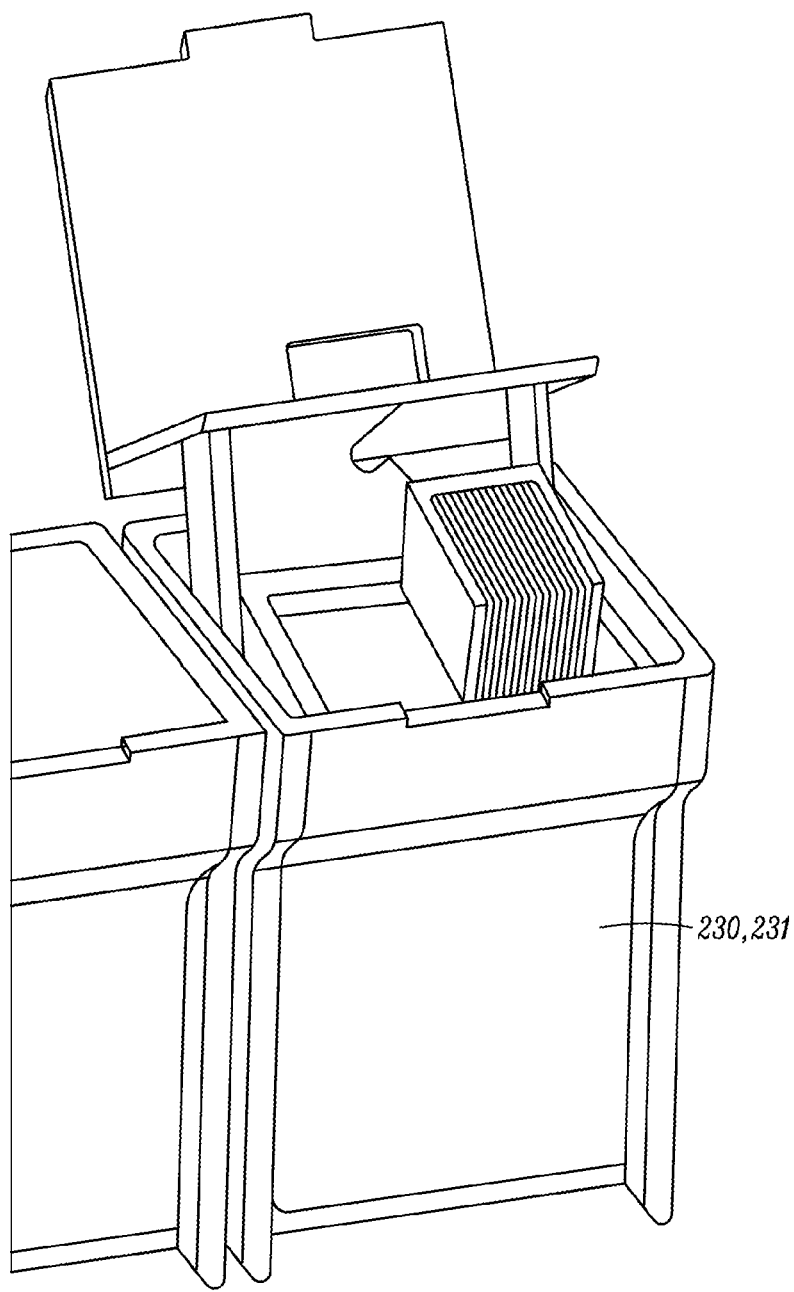
FIGS. 5A, 5B, 5C, 5D, and 5E.
Figure 5B:
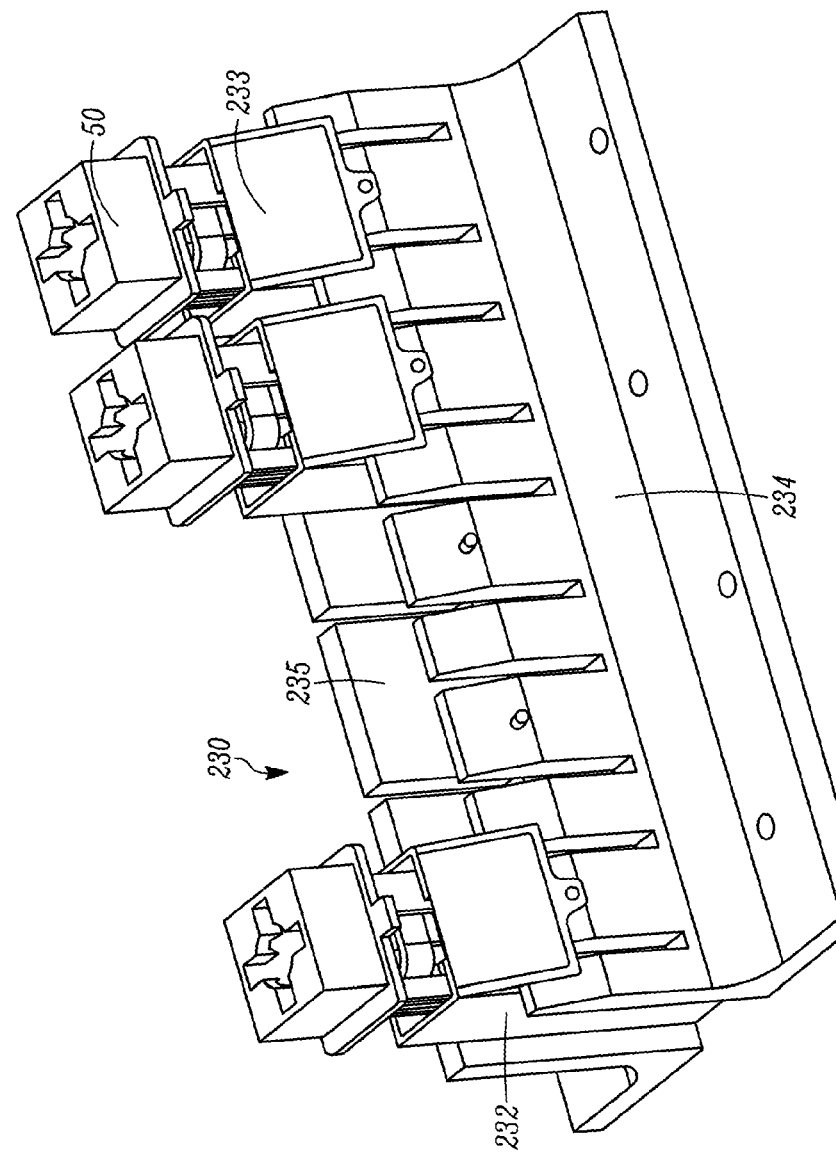
Figure 5C:
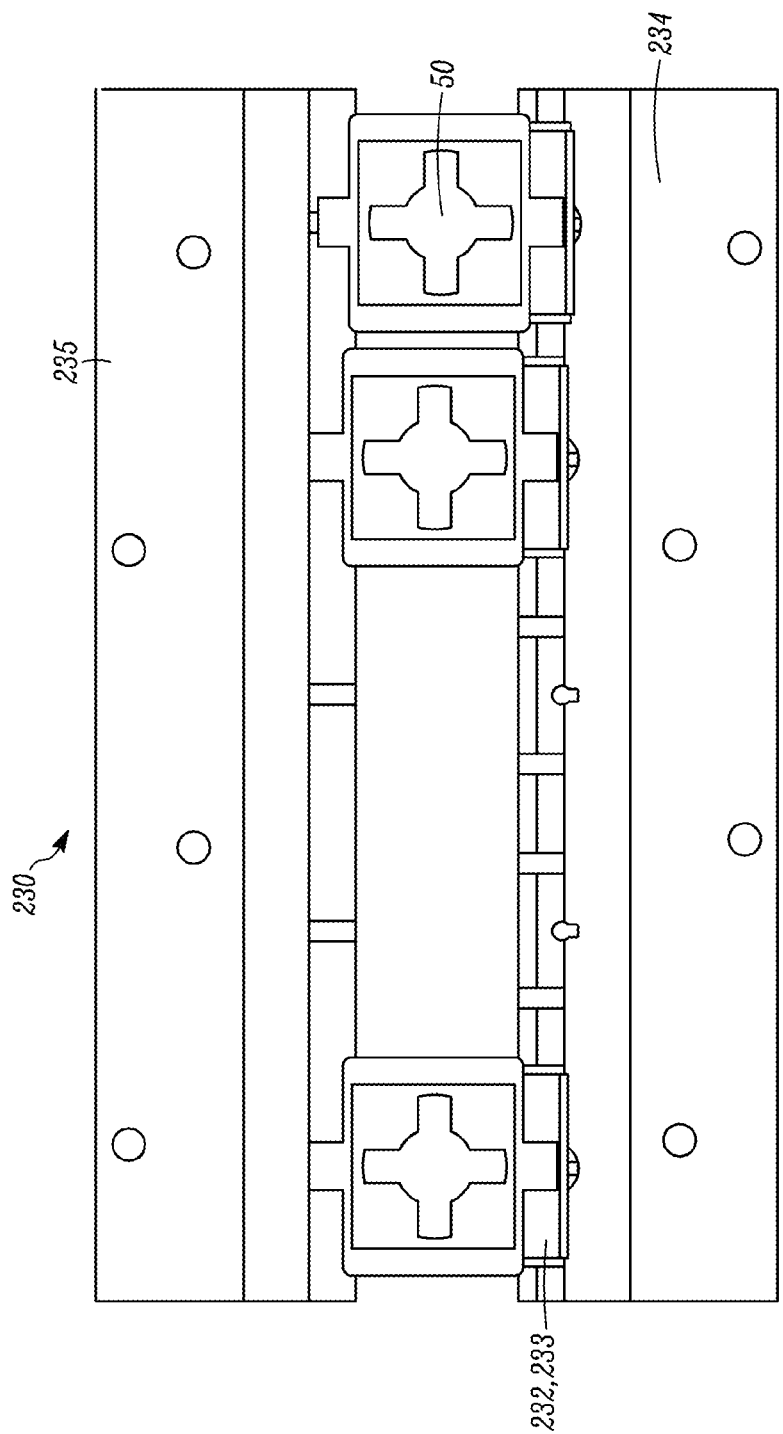
Figure 5D:
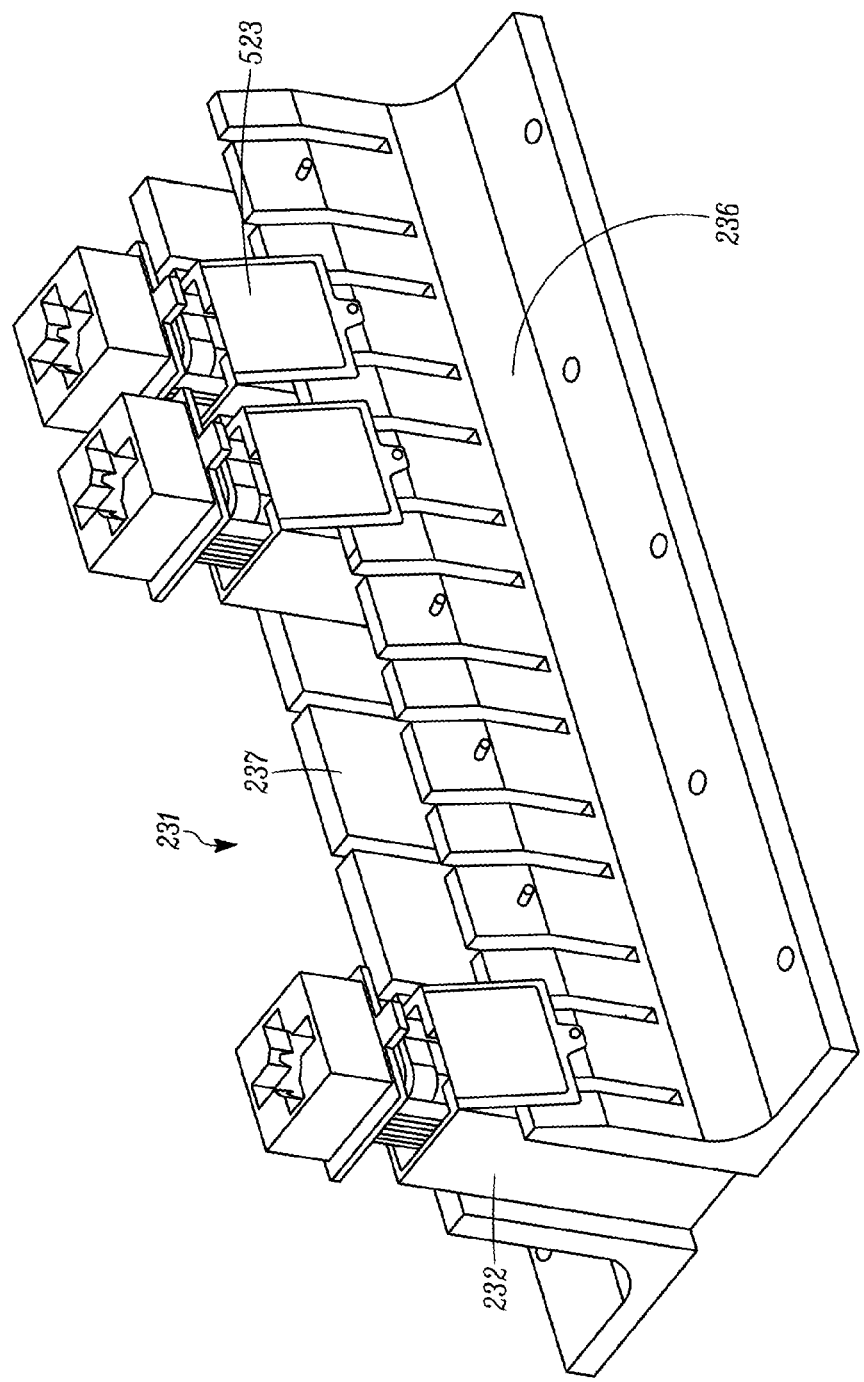
Figure 5E:
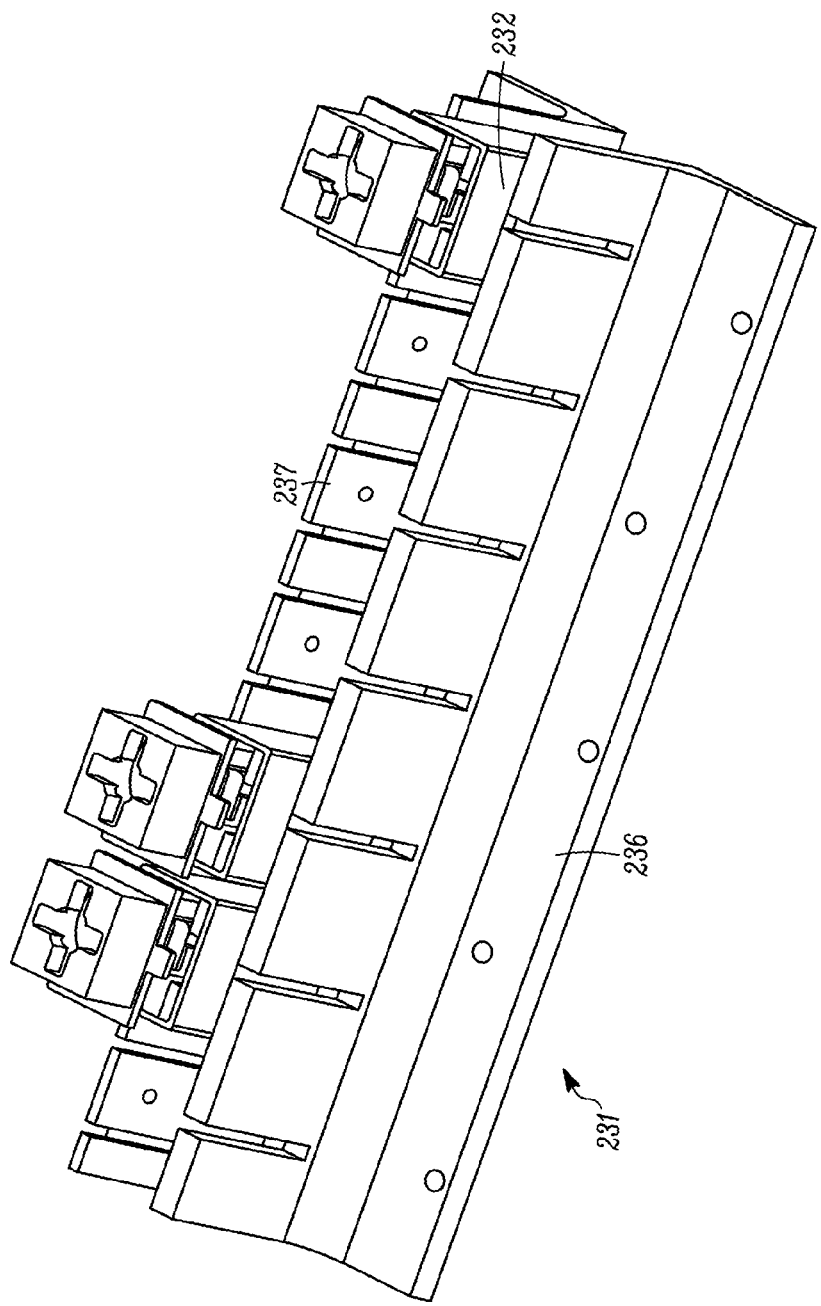

In particular embodiments, the reagent container rack 230, 231 includes at least one reagent container 232 (e.g. one, two, three, four, five, six, seven, eight, nine, ten, or more reagent containers). In certain embodiments, the reagent container rack 230, 231 is located on a shaker on the platform 211. The reagent container rack 230, 231 can include, e.g., primary antibodies and/or detection systems, e.g. a secondary antibody with an enzyme, a substrate to produce a colored reaction product via the enzyme, and/or counterstain. In an embodiment, the at least one reagent container rack includes a primary reagent container rack 230 and a secondary reagent container rack 231. For example, the primary reagent container rack 230 can include five reagent containers 232 and/or the secondary reagent container rack 231 can include 7 reagent containers 232. FIG. 5A illustrates an embodiment of the at least one reagent container rack 230, 231 which includes a lid. FIGS. 5B and 5C illustrate an at least one reagent container rack (e.g., a primary reagent container rack 230) configured to hold five reagent containers 232. The at least one reagent container rack includes a first member 234 and a second member 235 located opposite each other and configured to secure the five reagent containers 232 therein. FIGS. 5E and 5F illustrate an embodiment of the reagent container rack (e.g., a secondary reagent container rack 231) configured to hold seven reagent containers 232. The reagent container rack includes a first member 236 and a second member 237 located opposite each other and configured to secure the five reagent containers 232 therein.

Figure 6A:
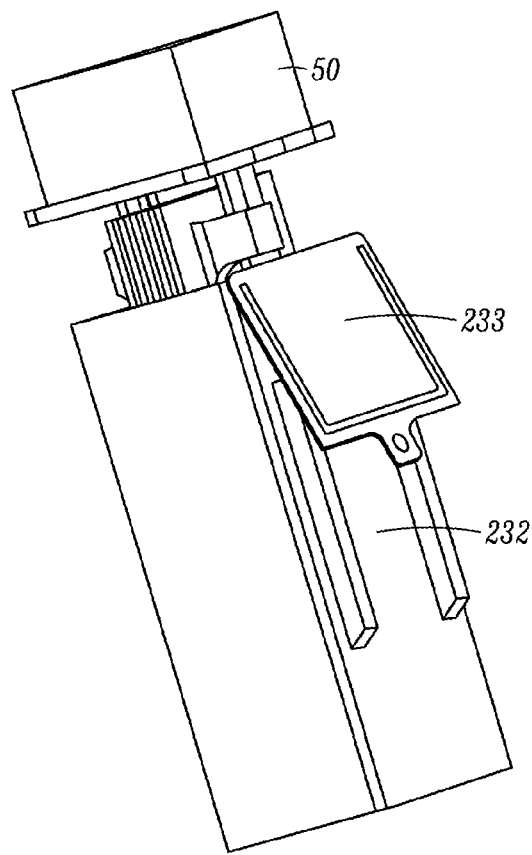
FIGS. 6A and 6B.
Figure 6B:
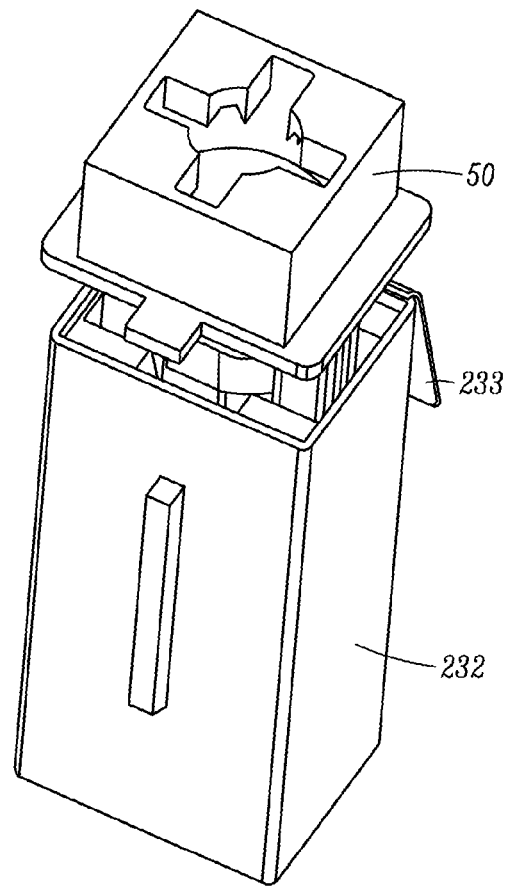
Figure 7A:
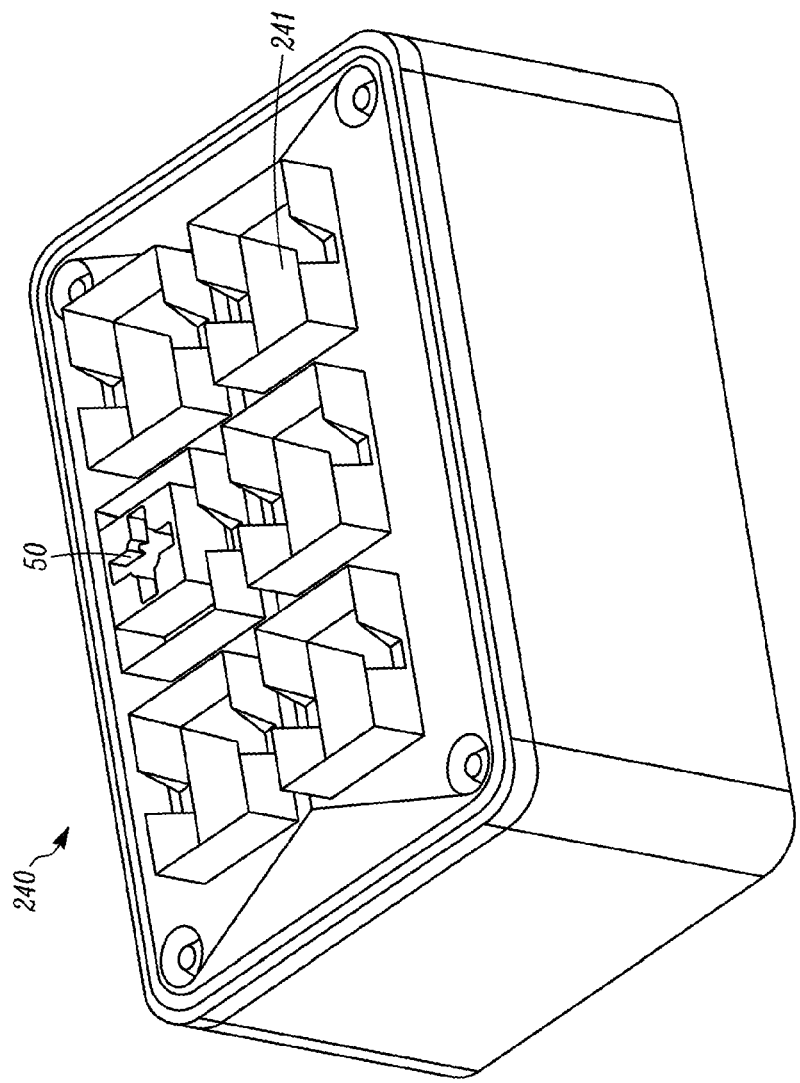
FIGS. 7A, 7B, 7C, 7D, 7E, and 7F.
Figure 7B:
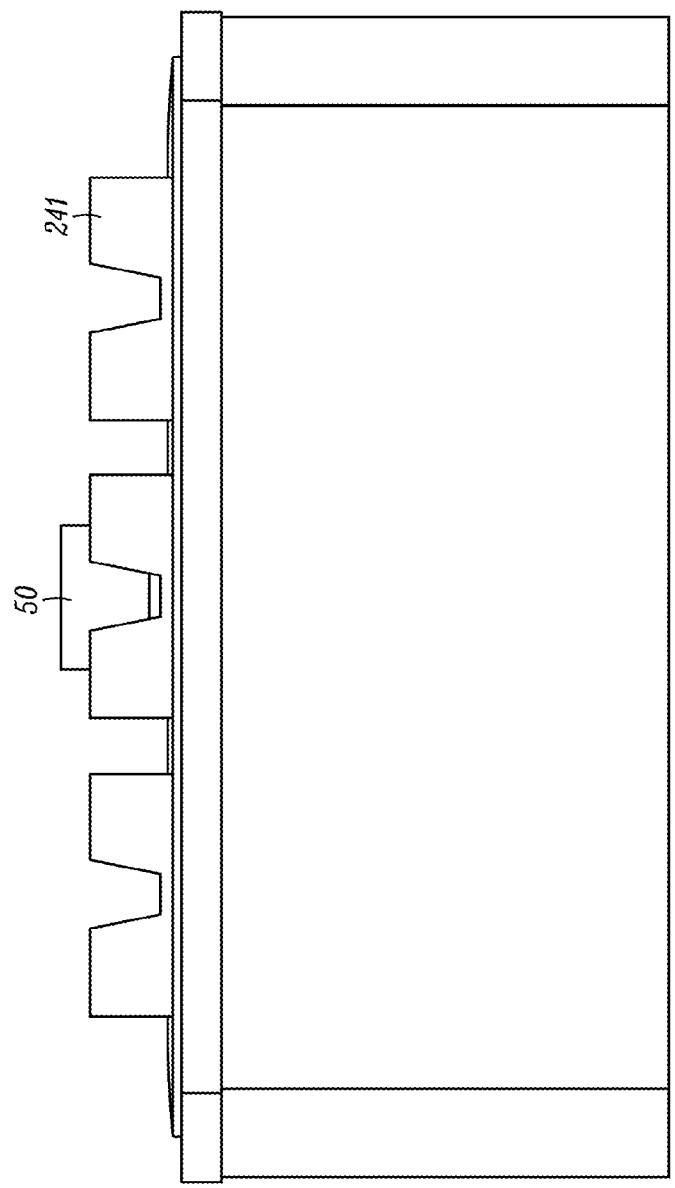
Figure 7C:
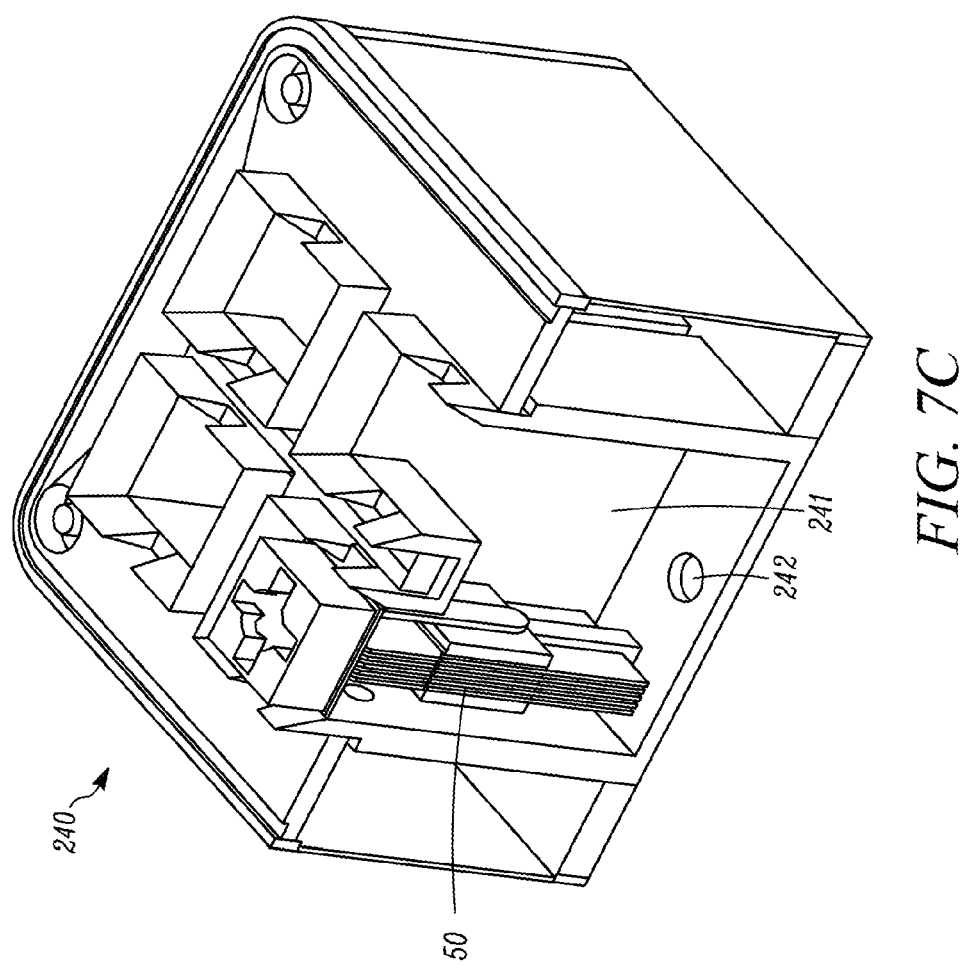
Figure 7D:
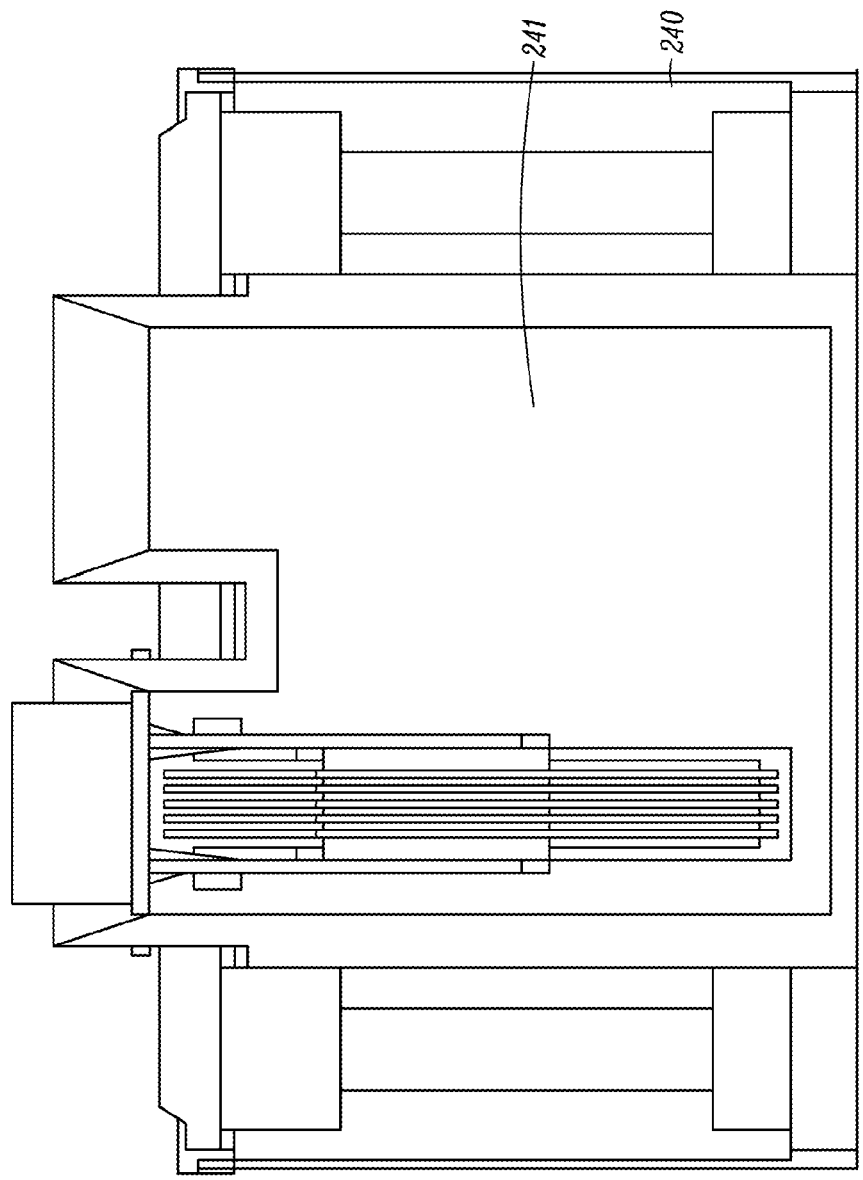
Figure 7E:
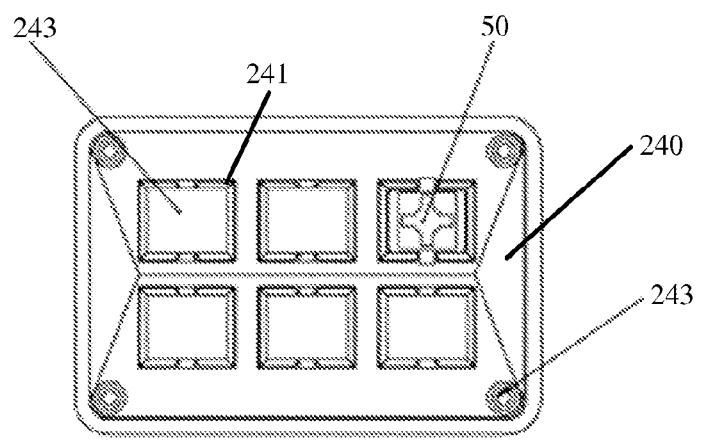
Figure 7F:
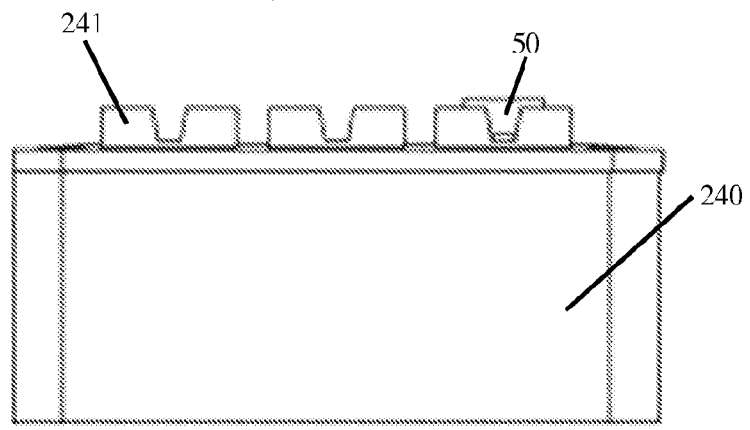

FIGS. 6A and 6B illustrate an embodiment of a reagent container 232. The reagent container 232 holds the reagents utilized in staining processes (for example, a primary antibody, a secondary antibody specific to the primary antibody and with a conjugated enzyme, a substrate specific to the conjugated enzyme, and a counterstain), and configured to receive a slide rack assembly 50, for example, from an opening located at the top of the reagent container 232. Each bath have a different reagent or have multiple reagents therein and can include a bar code label indicating the reagent contained therein. The reagent container can include a reagent container lid 233, which can produce a substantially water tight seal. For example, the reagent container lid 233 can be a snap-fit lid with a rubber seal to prevent leakage of the fluid therein. The reagent container 232 can include a coupling to lock the lid and/or align the reagent container 232 for correct orientation for slide rack assembly 50 insertion. Furthermore, the slide rack assembly may act as a reagent container cover when placed in the reagent container 232. That is, the slide rack lid 52 is configured to cover the reagent container 232 when slide rack assembly 50 is inserted in the reagent container 232.

The reagent container 232 can hold up to 25 mL of reagent, for example about 5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, about 20 mL, about 21 mL, about 22 mL, about 23 mL, about 24 mL, about 25 mL, or more of reagent. In an embodiment, the reagent container 232 holds about 15 to about 20 mL of reagent. A reagent container 232 can be of any size, shape, or volume appropriate for receiving a slide rack assembly and the associated microscope slides. The volume of the reagent in the reagent container 232 is sufficient to submerge the sample on the microscope slide(s). The reagent container need not include a reagent container lid.

In an embodiment, the processing fluid within a reagent container 232 (e.g., primary antibody, secondary antibody conjugated to an enzyme, a chromogen, a substrate, and/or counterstain) is used for multiple slide rack assemblies. For example, the processing fluid within a reagent container 232 can be used for 50 to 70 microscope slides, 50 to 65 microscope slides, 50 to 60 microscope slides, 50 to 55 microscope slides, 55 to 70 microscope slides, 55 to 65 microscope slides, 55 to 60 microscope slides, 60 to 70 microscope slides, 60 to 65 microscope slides, or 65 microscope slides. In another embodiment, the processing fluids within a reagent container 232 is used for 50, 51, 52, 53, 54, 55, 56, 57, 58, 58, 59, 60, 61, 62, 63, 64, 65, 66, 67, 68, 69, or 70 microscope slides.

In an embodiment, the a buffer wash tank assembly 240 includes at least one buffer wash stank 241, for example one buffer wash tank, two buffer wash tanks, three buffer wash tanks, or more. In an embodiment, each buffer wash tank 241 includes at least one slide rack assembly loading position 243, i.e. a position configured to receive a slide rack assembly 50. For example, FIGS. 7A, 7B, 7C, 7D, 7E, and 7F illustrate an embodiment of a buffer wash tank assembly 240 includes three buffer wash tanks 241, each having two positions configured to receive a slide rack assembly 50, as specifically shown in FIGS. 7C and 7D. Furthermore, in an embodiment, the buffer wash tank 241 includes a buffer wash tank drain 242 for draining wash buffer from the tank 241. For example, the wash buffer may be drained and replaced after washing 20-40 slides. In a certain embodiment, the wash buffer is replaced after washing 25-35 slides or after 30 slides. Furthermore, the wash buffer assembly 240 can include fasteners, e.g. screws, bolts, etc., for mounting the assembly to the platform 211.

Figure 8:
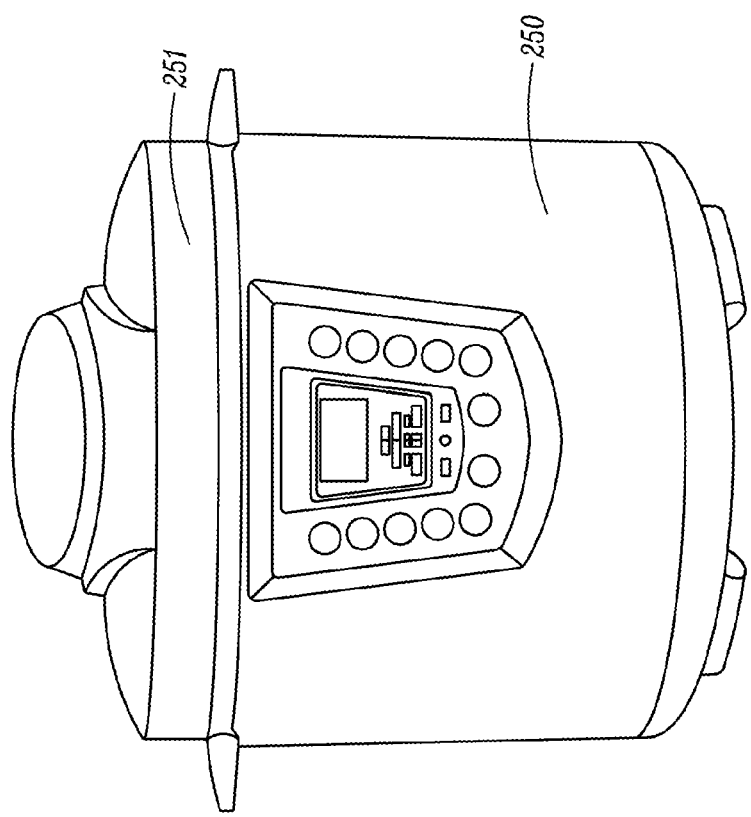
FIG. 8.

In another embodiment, the heating chamber includes a heating vessel 240, a heating vessel lid 241, and a heating element. See for example, FIGS. 3C and 8. The heating vessel 240 can include a small amount of liquid (e.g., water) that generates steam during the heating process, thereby increasing the internal pressure. In an embodiment, the heating chamber achieves a temperature greater than 100° C. The heating vessel 240 can include agent baths (not shown), for example one, two, three or more agent baths, that accept slide rack assemblies 50. The agent baths can include an antigen retrieval solution or agent for, e.g., immunohistochemistry staining.

In a particular embodiment, the heating vessel lid 241 can be opened and closed by the robotic arm, thereby allowing the addition and removal of slide rack assemblies 50 from the heating chamber. The heating vessel lid 241 can have an air-tight seal to create a pressurized internal chamber. For example, the heating chamber can become pressurized when the small amount of liquid within the heating vessel 240 evaporates in the air-tight heating chamber. In an embodiment, the at least one heating chamber includes a pressure cooker. The heating chamber may be of any size, shape, or volume appropriate for staining procedures.

In an embodiment, the heating chamber includes sensors and a data interface for transmitting sensor data to a central computer controller. The sensors can include temperature and/or pressure sensors. In certain embodiments, the Scheduler controls the pressure of the heating chamber.

In an embodiment, the antigen retrieval buffer is automatically aspirated before and after each run. Antigen retrieval buffer can automatically be dispensed in the agent bath before the slide rack assembly is placed in the agent bath.

Figure 9A:
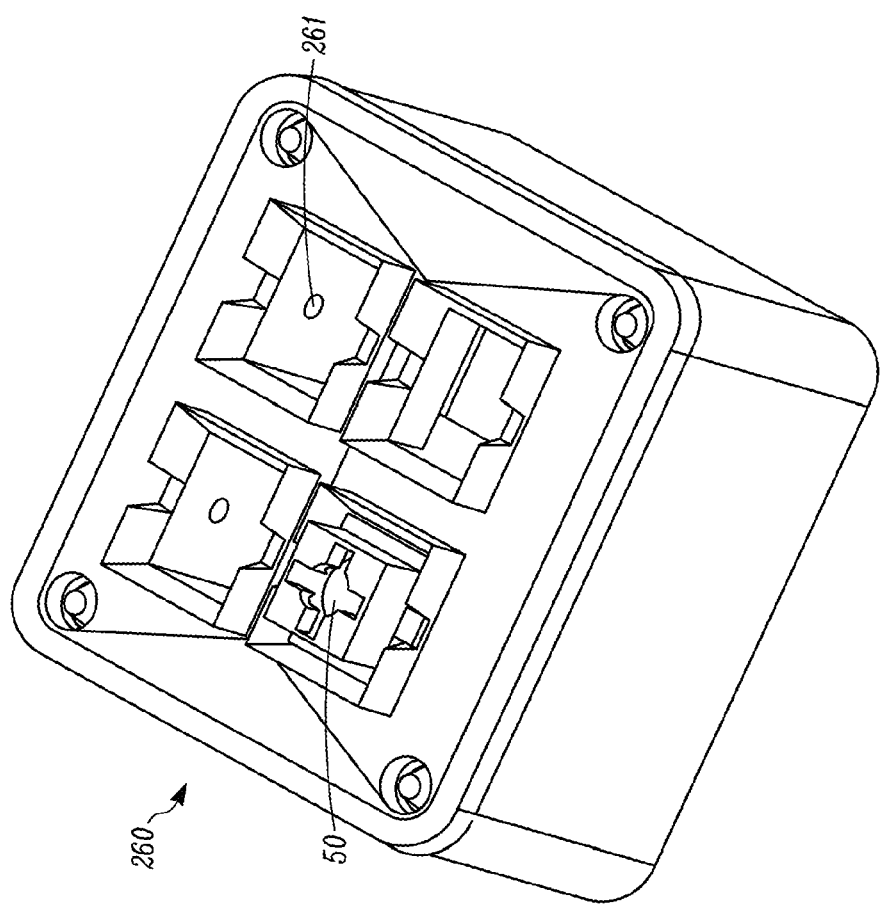
FIGS. 9A and 9B.
Figure 9B:
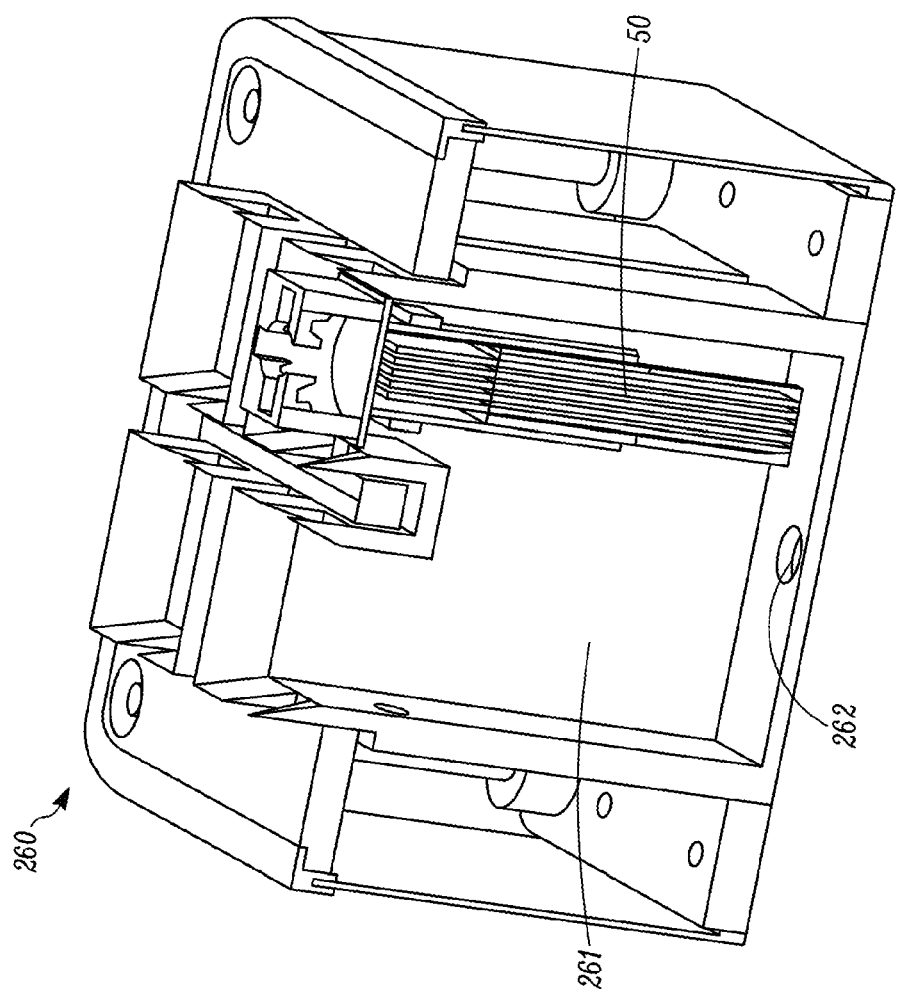
Figure 10A:
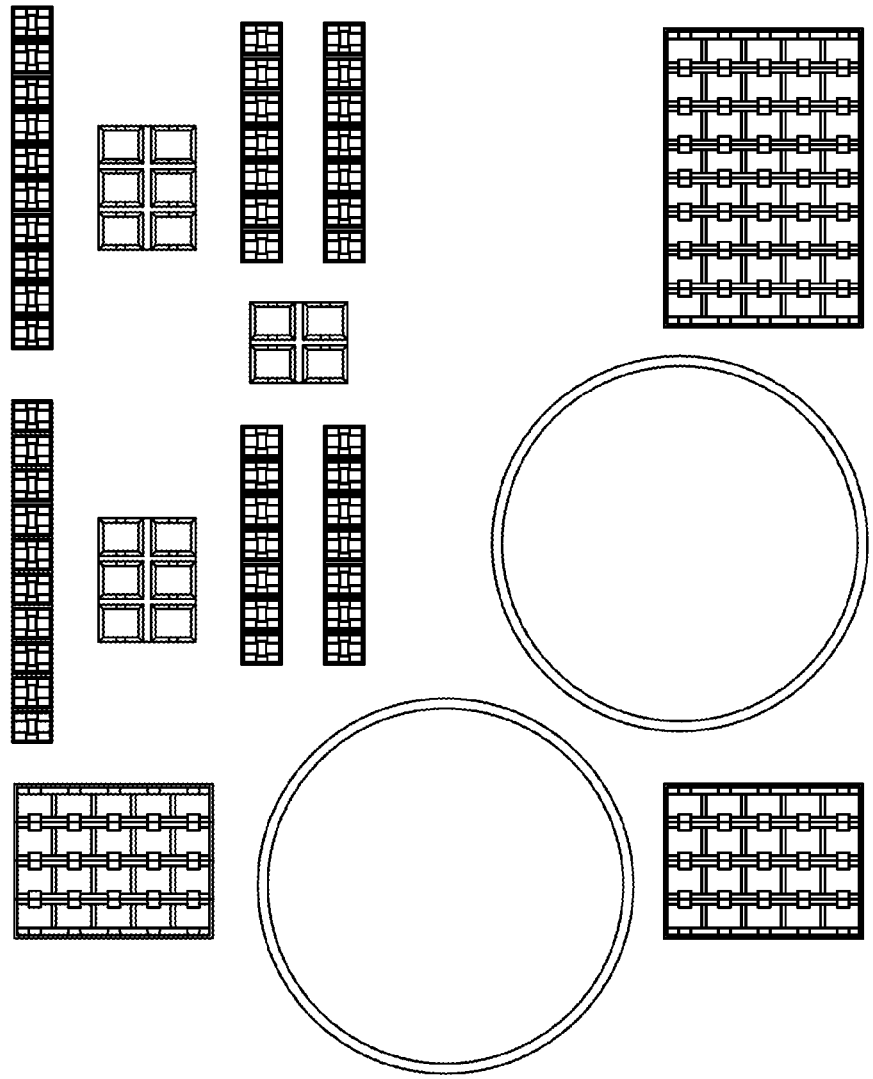
FIGS. 10A and 10B.
Figure 10B:
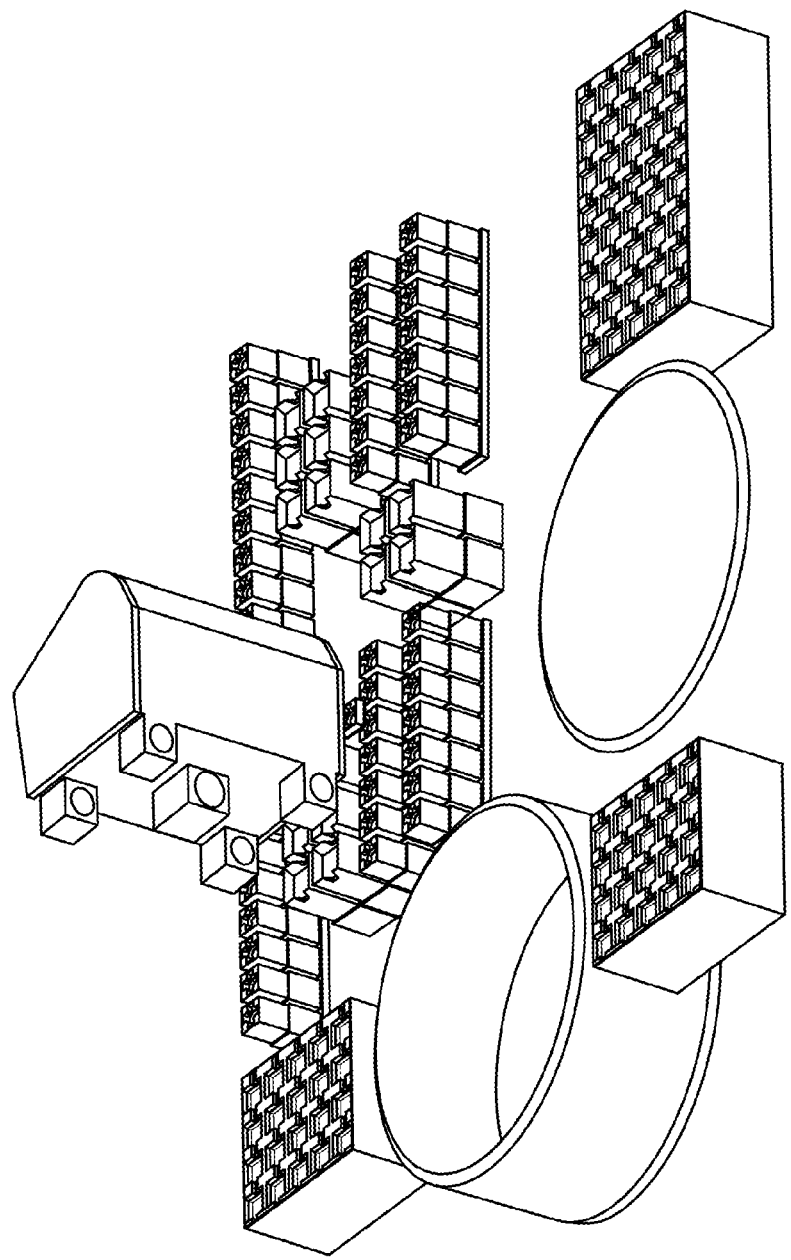
Figures 12A, 12B:
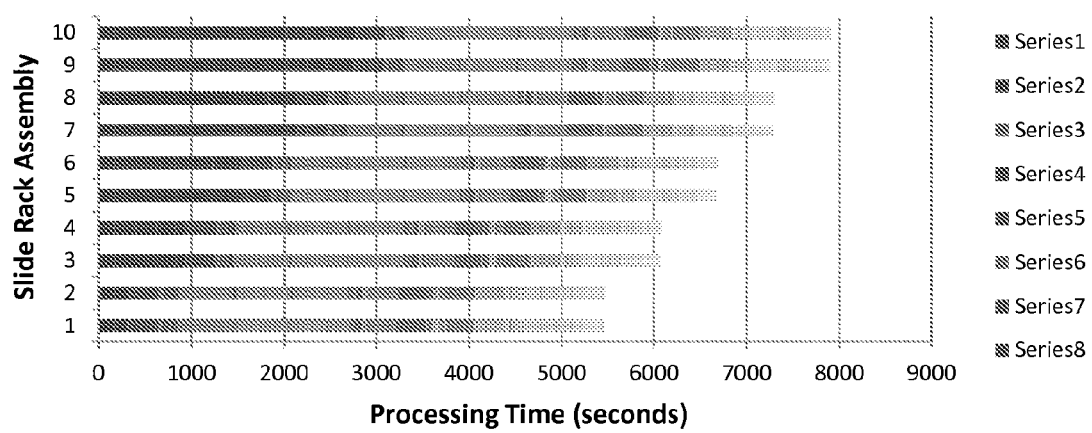
FIGS. 12A and 12B.

In an embodiment, the water wash tank assembly 260 includes at least one water wash tank 261, for example one water wash tank, two water wash tanks, three water wash tank, or more. In an embodiment, each water wash tank 261 includes at least one slide rack assembly loading position, i.e. a position configured to receive a slide rack assembly 50. For example, FIGS. 9A and 9B illustrate an embodiment of a water wash tank with two water wash tanks, each configures to receive two slide rack assemblies 50. Furthermore, in an embodiment, the water wash tank 261 includes a water wash tank drain 262 for draining wash water from the tank 261. In an embodiment, the water utilized in the water wash tank is deionized water. For example, the wash water may be drained and replaced after washing 20-40 slides. In a certain embodiment, the wash water is replaced after washing 25-35 slides or after 30 slides.

In an embodiment, the automated stainer 200 holds up to 20 slide rack assemblies 50, and each slide rack assembly holds up to 20 microscope slides, for a total capacity of up to 400 microscope slides. Alternatively, the automated stainer 200 can hold 5, 6, 7, 8, 9, 10, 11, 12, 13, 14, 15, 16, 17, 18, 19, 20, 21, 22, 23, 24, 25, 26, 27, 28, 29, 30, or more slide rack assemblies 50. For example, the automated stainer 200 holds up to 20 slide rack assemblies 50, and each slide rack assembly holds up to 5 microscope slides, for a total capacity of up to 100 microscope slides.

The bar code reader 16 can be positioned to scan bar codes, for example on the slide racks assembly 50, the reagent container 232, the buffer wash tank 241 or assembly 240, the water was tank 261 or assembly 261, and/or the holding rack 222.

In an Immunohistochemistry method, one of the processing fluids is an antibody contained in a reagent container. The antibody is unique because different slides will be treated with different antibody solutions such that multiple different antibodies will typically be used during the staining process. Each slide rack is dedicated to a different antibody. The slide rack has a slot for holding a unique bar code label to link the slide rack with a specific antibody. As discussed above, the top of the slide rack also functions as a lid for the antibody bath during incubation.

As discussed above, the slide rack assembly is comprised of an open frame containing the slides, such that the slide rack can be submerged into a reagent container 232 and the processing fluids contained therein will then contact the slides. The slide rack assembly contains a slide rack lid 52 that acts as a lid to the reagent bath when the slide racks are placed within the reagent baths. Each slide rack assembly contains a bar code that identifies the unique antibody that is designated for all of the microscope slides 100 contained therein.

In an embodiment, the automated stainer automatically drains and refills the bulk fluids (e.g., wash buffer, water, etc.) once every 24 hours. For example, the automated stainer can automatically drain bulk fluids at the end of the day and automatically fill the bulk fluids at the beginning of the day, or at any other appropriate time points.

Bar Code Reader

Each reagent container 232 can contain within its label a bar code that identifies certain information about the reagent including at least one of (1) reagent name, (2) reagent code number, (3) reagent lot number, (4) reagent expiration date, and (5) number of runs left.

Each microscope slide 100 can contain a bar code within its label that identifies certain information about the biological sample attached to the slide including at least one of (1) patient name, (2) patient number, (3) tissue type, and/or (4) immunohistochemical staining protocol to be applied to that slide.

Each slide rack assembly 50 can contain a bar code within its label that identifies certain information about the staining procedure to be performed on the slides contained therein. For example, the certain information can include required processing fluids and the required incubation for each processing fluid.

The bar code reader 16 of the automated stainer 200 is capable of reading bar code information and sending the bar code information to the computer processor for decoding. In an embodiment, the bar code reader 16 is attached to the mechanical robotic arm 10. The bar code reader 16 is a device that reads information from a label and uses that information to identify the information about the object containing the label. The information associated with a microscope slide 100, for example, may be a patient name, patient number, tissue type, and/or staining protocol. The information associated with a slide rack assembly 50, for example, is a staining protocol. The information associated with a reagent container, for example, may include reagent name, reagent number, lot number, expiration date, and/or number of tests remaining. The bar code reader 16 can transmit this information to a central computer that would then use this information to process the slides.

The bar code reader could be any type of reader capable of collecting information from a label. Such information could be presented in the form of a traditional bar code (2-D bar code), a 3-D bar code, a higher complexity design, sometimes described as an infoglif, or an optical character recognition device (OCR) that is capable of directly reading alpha-numeric characters.

Graphical User Interface

The graphical user interface (GUI) is a component of the software that accepts input from the user. The GUI can accept input from the user that initializes the instrument, accepts user input for identifying biological samples for purposes of initiating a staining run.

The Graphical User Interface is typically the portion of the software that is presented to the user in the form of a graphical display, such as through a computer monitor. The GUI may also accept input from the user typically in the form of keyboard strokes or through pointing devices, such as a mouse. GUI's are standard components of most computer systems that require user input. The GUI provides an interface for the user to control the automated stainer 200. The GUI can also present information to the user by means of a monitor display. Such information may include status reports and Scheduler information.

The GUI could be of any design capable of accepting user input into the system, and provides the user with status information regarding the ongoing processes.

Robot Controller Software

The robotic controller software is a component of the software that controls the mechanical components of the instrument, such as robotic movements, pump activation, waste disposal.

The robot controller software is the component of the software that creates an interface between the computer and the mechanical, electrical, optical, and fluidic elements of the automated stainer 200. The controller software may activate certain mechanical activities, such as turning on or off a pump (e.g., the liquid lump 214), moving the robotic arm 10 to immerse the slide rack assembly 50 into wash tanks 241, 261 or to move slide rack assemblies to the reagent containers 232, turning on or off heating elements (e.g., the heating element of the heating chamber 250, 251), opening or locking a reagent container lid 233 or a heating vessel lid 231.

The controller software is an integral component of the instrument, but the exact design and architecture of the software is not essential to its operation, so long as it can achieve the primary goal of controlling the mechanical elements of the automated stainer 200.

Scheduler Software

The Scheduler Software is a software component that schedules the activity of the instrument and is required to coordinate the processing of multiple staining sequences on multiple slides simultaneously. The Scheduler allows for continuous mode and batch mode processing while optimizing the run-time for rapid throughput.

Scheduler Software is required to determine the sequence of operations in a most time efficient manner of moving, incubating, and removing slides from the processing fluids. The efficiency of the Scheduler will determine the run-time for processing the slides from beginning to end. The Scheduler determines the most efficient way of processing the slides. The Scheduler will also provide the user with status information throughout the run.

The Scheduler must take into account all of the processing steps, incubation times, speed at which the robot can complete its tasks, number of slide racks being processed, number of unique antibodies. In order to calculate the optimal run-times, sequence, and timings, the scheduler will contain a specified logic, sometimes referred to as an algorithm. There are multiple ways in which an algorithm could be designed to accomplish essentially the same tasks.

Figure 11:
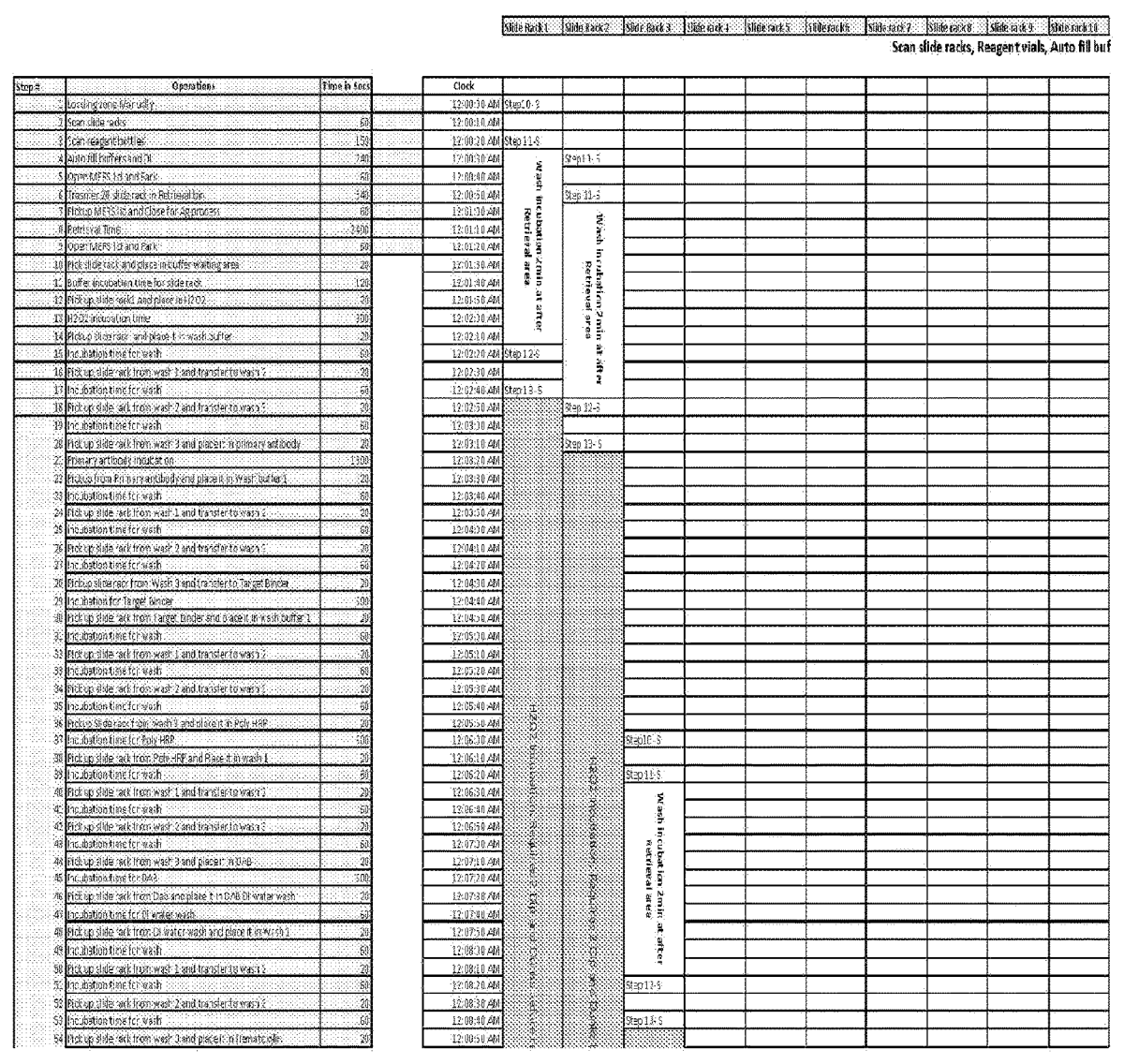
Figure 11:
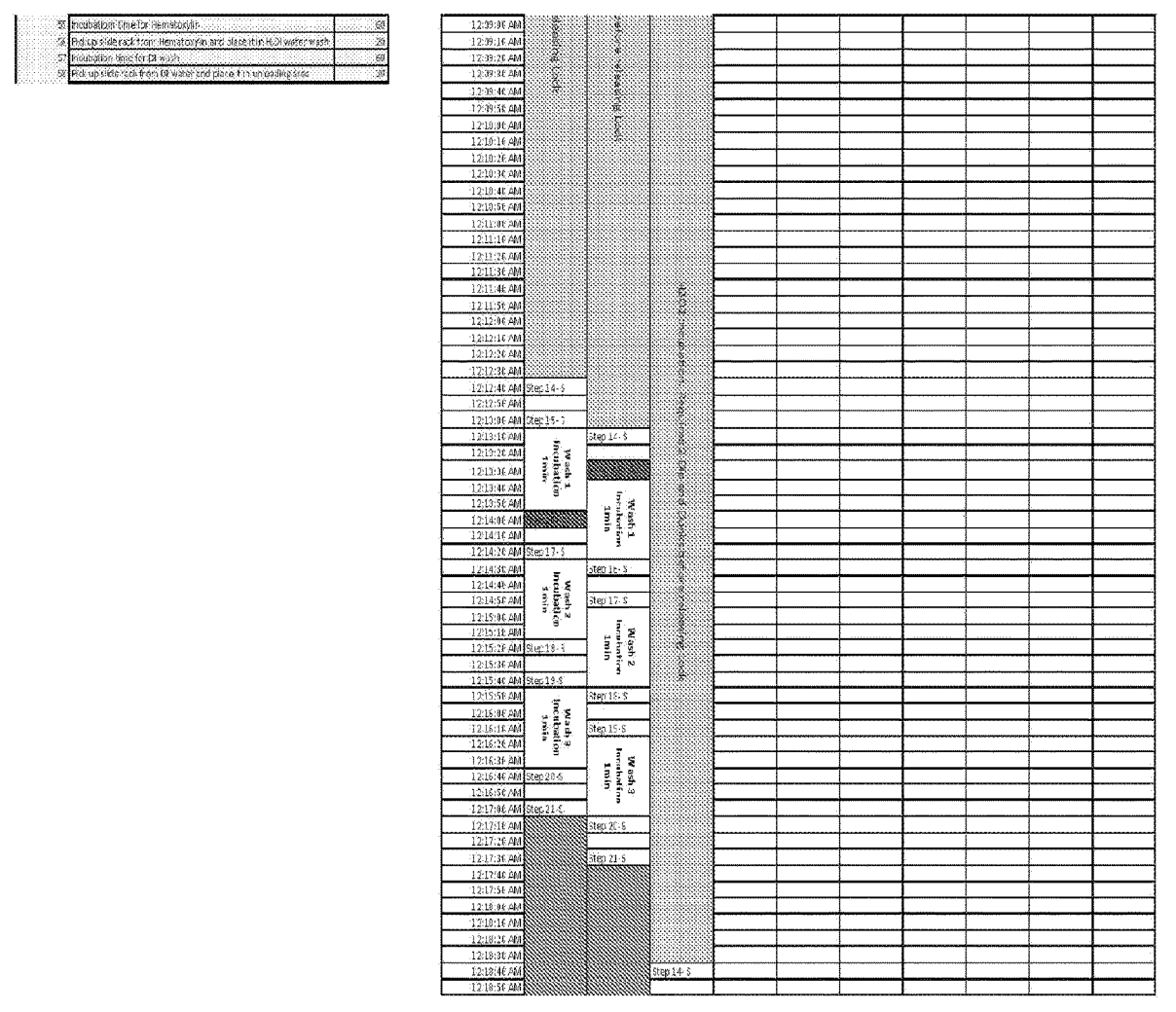
Figure 11:
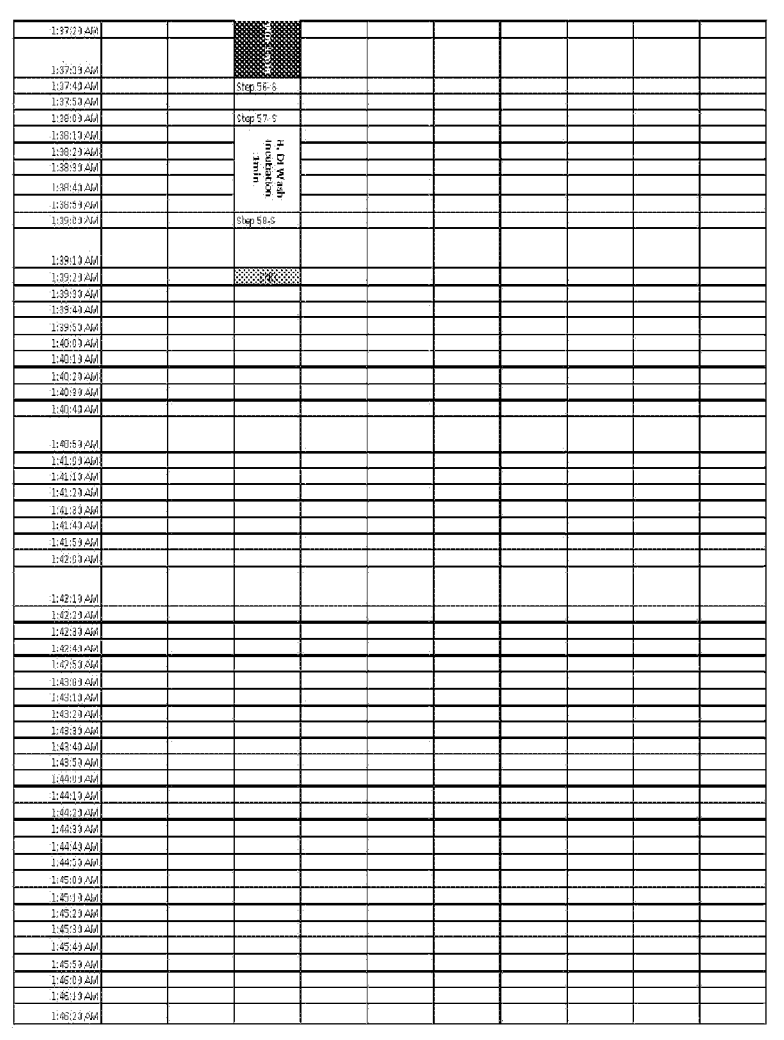

FIG. 11 illustrates an example of sequence of operations for three slide rack assemblies to proceed through staining protocols on the automated stainer 200.

Connections of Main Elements and Sub-Elements of Invention

The method of performing immunohistochemistry is a process designed to stain a biological sample. The stained biological sample can then be viewed by light microscopy by one trained in the method, such as a pathologist. The information provided by the stain may allow the pathologist to distinguish cancer from non-cancer, or may aid in the identification of specific types or subtypes of cancer. In other embodiments, immunohistochemistry may be able to identify the causative agent in certain infectious processes.

The method of immunohistochemistry begins with a biological sample attached to a microscope slide. The microscope slide has been standardized as glass rectangle of about 1 inch by 3 inches. There are multiple types of microscope slides commercially available, and the microscope slide is not a part of the present invention.

Multiple microscope slides are typically stained at the same time by immunohistochemistry. This is commonly referred to as a run. Each microscope slide may contain tissue from a different patient, or may contain tissue from the same patient that is going to be tested in a different way.

The microscope slides are grouped together within a slide rack assembly 50. The function of the slide rack is to hold multiple microscope slides that are going to be processed within a single run (i.e., receive the same treatments). The slide rack assembly provides the means for interfacing the microscope slides with the various processing fluids that are necessary to perform the immunohistochemistry method. The slide rack assemblies provide the interface for placing the microscope slides into the reagent baths.

The processing fluid baths contain the processing fluids that must contact the biological samples on the microscope slides in order for the staining method to proceed. There are various types of processing fluids that must be applied in a specific sequence for a specified time interval. The first processing fluid is typically call an antigen retrieval, and this step is unique compared to the subsequent steps, in that antigen retrieval must be performed at a high temperature.

The heating chamber 250, 251 provides the high temperature conditions necessary for performing antigen retrieval. In an embodiment, the antigen retrieval proceeds at temperatures greater than 100° C. Because water boils at temperature around 100 C, it is difficult to produce temperatures in aqueous solutions of greater than 100 C, unless a pressurized system is used. Under pressure the boiling point of water can be increased. For example at a pressure of 10-15 psi, the boiling point of water is approximately 110-121° C. The heating vessel 250 accepts the reagent baths containing the slide rack assembly 50, containing the microscope slides 100 and associated biological samples, and exposes the biological samples to an elevated temperature for a sufficient length of time to complete the antigen retrieval process.

The mechanical robot contains a grip assembly 11 that moves in the x, y, and z dimensions. The arm also engages other elements of the invention, such as the slide rack assembly 50, the slide rack lid 52, and the lid of the heating chamber 251. This allows the mechanical robotic arm 10 to open and close lids, e.g. the heating chamber, and to move the slide racks into and out of the various reagent baths containing the processing fluids. For example, the robotic arm can open the heating chamber lid 241, place at least one slide rack assembly 50 into an antigen retrieval bath in the heating chamber 240, and lock the heating chamber lid 241 for antigen retrieval. In an embodiment, the heating chamber 240 can include a high pH retrieval buffer and/or a low pH retrieval buffer. In certain embodiments, the heating chamber 240 includes Alternative Embodiments of Invention In contrast to previous strainers, embodiments of the present disclosure use a different approach. The slides are grouped together within slide rack assemblies so that each slide rack assembly is placed into a reagent bath, all slides within the slide rack receive the processing fluid simultaneously. This type of processing could be described as batch-mode processing. Furthermore, as a first slide rack completes its incubation within a reagent bath and is removed from the reagent bath, a second slide rack can be introduced into the vacated reagent bath. This process can be continued indefinitely by moving a series of slide racks through a series of reagent baths, one after another. This type of process could be described as continuous flow and is significantly more efficient than previous stainers.

Operation of Preferred Embodiment

Present disclosure describes a method for manipulating microscope slides containing mounted biological specimens for the purpose of processing, staining, and evaluating said biological specimens in order to extract relevant information from the sample (e.g., a biological sample, a cell or a tissue sample), such as molecular information. The invention utilizes an automated stainer that facilitates the addition and removal of various processing fluids that come into contact with the biological samples.

One method of staining molecular structures in tissues is by a process known as immunohistochemistry. An important part of this procedure is a series of steps whereby processing fluids are contacted with the biological sample. This invention describes a novel method in which processing fluids come into contact with the biological sample mounted onto microscope slides. Processing fluids can be added to (i.e. brought into contact with) the slides by dipping the slides into a bulk solution such that the slides are completely immersed in the processing fluid (e.g. a reagent in a reagent container), leaving the slides in the processing fluid for a length of time necessary for the desired molecular reaction to occur, and then removing the slides from the bulk fluid. This sequence is facilitated by a mechanical robotic arm that can manipulate a slide rack assembly containing multiple microscope slides. After the appropriate reaction has taken place, the slide rack assembly (and the slides therein) are removed from the reagent container, and the slide rack assembly (and the slides therein) are moved to the next bulk container of processing fluids (e.g., a buffer wash tank or a water wash tank). This sequence of steps of moving slides into a processing fluid, incubating, and removing slides from the processing fluids, forms the basic reaction step that is repeated multiple times with different processing fluids until the final reaction has been achieved.

Immunohistochemistry is a method for testing a biological sample (e.g. cells or tissue samples) for the presence of specific molecules. These methods are useful in both research and diagnostic applications for analyzing cell or tissue specimens. For example, in a diagnostic setting the molecular profile of a tissue can provide evidence of a particular disease state, such as cancer. These methods comprise preparing an antibody to the particular molecule of interest.

The term "antibody" as used herein refers to immunoglobulin molecules and immunologically active portions of immunoglobulin (Ig) molecules, i.e., molecules that contain an antigen-binding site that specifically binds (immunoreacts with) an antigen, comprising at least one, and preferably two, heavy (H) chain variable regions (abbreviated herein as VH), and at least one and preferably two light (L) chain variable regions (abbreviated herein as VL). Such antibodies include, but are not limited to, polyclonal, monoclonal, chimeric, single chain, Fab, Fab', and F(ab')2 fragments. The VH and VL regions can be further subdivided into regions of hypervariability, termed "complementarity determining regions" ("CDR"), interspersed with regions that are more conserved, termed "framework regions" (FR). Each VH and VL is composed of three CDR's and four FRs, arranged from amino-terminus to carboxy-terminus in the following order: FR1, CDR1, FR2, CDR2, FR3, CDR3, FR4. In general, antibody molecules relates to any of the classes IgG, IgM, IgA, IgE and IgD, which differ from one another by the nature of the heavy chain present in the molecule. Certain classes have subclasses as well, such as $IgG_1$, $IgG_2$, and others. Reference herein to antibodies includes a reference to all such classes, subclasses and types of antibody species.

The specificity of antigen-antibody binding allows an investigator to infer the presence of the antigen (target molecule, or target) whenever the antigen-antibody reaction takes place. For example in the diagnosis of cancer, a specific antibody to a cancer-associated antigen is placed in contact with cells or tissue sample suspected of being cancer. If the antigen-antibody reaction occurs, this indicates that the suspected tissue was in fact cancer. Examples of this method are described below.

In an embodiment, the method of performing immunohistochemistry includes:

1. Fixing a tissue by placing a tissue into a fixative such as formalin. The fixative has two primary effects. First, it rapidly stops all metabolic activity in the cells so there is no degradation of molecular structures or changes in morphology, and secondly it makes the tissue rigid so that it can be embedded in hot paraffin and still retain its overall structure. Fixation with formalin is accomplished by inducing chemical cross-linking within and between molecules, particularly protein molecules.

2. Embedding the fixed tissue in hot paraffin which is allowed to cool to form a solid paraffin block containing the embedded tissue.

3. Cutting thin slices of the tissue from the paraffin block.

4. Applying a thin tissue section onto a microscope slide such that the tissue can be subsequently examined under the microscope once the staining reaction has been completed.

5. Treating the microscope slide with the attached tissue with a processing fluid that contains a paraffin solvent, such that the paraffin that is used to embed and mount the tissue onto the microscope slide is removed. Then treating the microscope slide with a series of alcohols to remove the paraffin solvent, and finally treating the microscope slides with a series of aqueous solutions to rehydrate the tissue back into its native state. These steps, call deparaffinization, effectively remove the paraffin, while leaving the tissue rehydrated and adherent to the microscope slide.

6. The next step involves applying an antigen retrieval solution to expose antigens within the tissue. In the process of fixing the tissue, the molecular structure of the protein is frequently altered such that an antibody reagent will no longer react with its target molecule. In order to overcome this limitation, antigen retrieval methods were developed that reverse the cross-links and restore the molecules to a more native configuration such that the antigen can be recognized by the antibody reagent. This step of the process is called heat-induced antigen retrieval, or simply antigen retrieval.

7. Treating a tissue on a microscope slide with a chemical to block endogenous enzyme activity.

8. Applying a specific antibody (e.g., a primary antibody) onto a tissue sample.

9. Allowing the primary antibody enough time to bind to its antigen (if present).

10. Visualizing the bound primary antigen by adding an enzyme linked to a secondary reagent.

11. Adding a substrate/chromogen which reacts with the enzyme to form a colored (dye) end-product.

12. Visualizing the colored end-product by viewing the tissue sample under the microscope.

Any of the preceding steps may be followed and/or preceded by a wash step, e.g. a wash buffer or water. If the colored end-product is observed, then the tissue contained the suspected antigen. If no colored end-product is observed, then the tissue did not contain the suspected antigen.

The concept of the present disclosure uses bulk fluid container to process multiple microscope slides simultaneously with the processing fluids. Furthermore, the present disclosure can move a series of slides racks and associated microscope slides through a series of processing fluids, with each slide rack following behind the preceding slide rack. This method of staining can be described as batch staining and continuous flow staining. These methods are unique among automated immunohistochemistry stainers. Batch method and continuous flow staining can process more slides in a markedly shorter time frame, and thus substantially improving upon existing automated immunohistochemistry stainers.

The software controlling the robotic movements contains a module called the Scheduler. Because the slides are processed through multiple processing fluids the Scheduler is determines the most efficient manner of moving, incubating, and removing slides (i.e. slide rack assemblies) from the various processing fluids. The Scheduler determines the most efficient way of processing the slides, such that runtimes are typically reduced by about 50% compared to other stainers currently being used for immunohistochemistry.

Step by step Process and Specifications.

Process: Following steps are required to complete the staining run.

1. Loading Slides:

A: Required Parts:

A: Slide Rack Assembly.

B: Slide rack holder bin.

C: Bar code labels for slide rack(s).

Details: A: Slide Rack:

1. Slide rack assembly should hold up to, e.g., five slides in vertical position.

2. Once the slides are loaded vertically, the slide rack lid with the help of movable hinge should be made upright with a grooved gentle locking system.

3. The same slide rack lid can also work as reagent bath lid during incubation steps.

4. The top of the slide rack lid (outer slide) will have a locking system (e.g., a clock and anti-clock wise locking system), which is operated by robotic arm.

5. Also the slide rack lid should have a space to place a bar code label.

6. The slide rack body will house, e.g., up to 5 slides vertically. Each slide is separated by a slide groove so that the slides do not come into contact with each other.

7 The slide rack body can include a linear thin strip with grooves on it to separate individual slides.

8. The material of the slide rack should be resistant to solvents, such as xylene and alcohol.

Process.

1. The user will load all processing fluid baths (e.g., reagent racks holding reagent baths such as primary antibodies, detection systems, etc.) onto the automated stainer with their lids open.

2. The robotic arm 10 with attached bar code reader 16 scans each of each of the processing fluid baths to determine location and types of processing fluids loaded.

3. After scanning, the mechanical robotic arm 10 releases the pressure valve and then opens the lid to the heating chamber 250, 251.

4. Agent baths will be filled with appropriate antigen retrieval solutions from bulk tanks.

5. The robotic arm 10 picks up the slide rack assembly from slide rack assembly loading area and places each slide rack assembly in the appropriate antigen retrieval agent bath.

6. The robotic arm 10 will close the heating vessel lid and lock the heating chamber.

7. Then the pressure valve will be pushed towards pressure.

8. The heating cycle will initiate.

9. Once the heating cycle is done the robotic arm 10 releases the pressure valve and opens the heating vessel lid.

10. The robotic arm picks up the slide rack assembly and places them into the next processing fluid.

11. The robotic arm picks up the slide rack assembly and transfers each slide rack assembly sequentially into the following processing fluids.

A. Hydrogen peroxide.
  B. Optionally, a protein block.
  C. Primary antibody.
  D. Secondary antibody with enzyme.
  E. Substrate to produce colored reaction product.
  F. Counterstain.

It is understood that the detailed examples and embodiments described herein are given by way of example for illustrative purposes only, and are in no way considered to be limiting to the invention. Various modifications or changes in light thereof will be suggested to persons skilled in the art and are included within the spit and purview of this application and are considered within the scope of the appended claims. For example, relative quantities of items may be varied to optimize the desired effect, additional items may be added, and/or similar items may be substituted for one or more of the devices describes. Those skilled in the art will recognize that many variations are possible within the spirit and scope of the invention in which all terms are meant in their broadest, reasonable sense unless otherwise indicated. Additional advantageous features and functionalities associated with the systems, methods, and processes of the present disclosure will be apparent from the appended claims. The terms, descriptions and figures used herein are set forth by way of illustration only and are not meant as limitations. Any headings utilized within the description are for convenience only and have no legal or limiting effect.

Specific Embodiments

According to an aspect of the disclosure, an automated stainer is disclosed. The automated stainer comprising: a plurality of slide rack assemblies with locations for multiple microscope slides; a plurality of processing fluid baths, each comprising a processing fluid; a robotic arm with a robotic head that releasably grasps the at least one slide rack assembly; and a processor that determines timing and movement of the robotic arm to move the plurality of slide rack assembly between the processing fluid baths.

In an embodiment, the processor comprises non-transitory computer readable medium storing a program to time and move the robotic arm based on the plurality of processing fluids.

In another embodiment, the plurality of processing fluids includes at least one of: antigen retrieval agent, at least one detection reagent, a wash buffer, and water. The at least one detection reagent can be at least one of a primary antibody, a secondary antibody specific to the primary antibody with a conjugated enzyme, a substrate specific to the conjugated enzyme, and a counterstain.

In certain embodiments, the at least one detection reagent is a plurality of detection reagents.

In an additional embodiment, the plurality of processing fluids are used for multiple slide rack assemblies.

In an embodiment, the antigen retrieval agent is in a heating chamber with a locking heated chamber lid.

In a certain embodiment, the robotic arm locks and unlocks the locking heated chamber lid.

In some embodiments, the robotic arm dispenses antigen retrieval agent to an antigen retrieval rack in the heating chamber and water to the heating chamber.

In an embodiment, the robotic arm is mounted on a robotic arm gantry.

In a certain embodiment, the robotic arm gantry and robotic arm facilitate movement three dimensionally.

In certain embodiments, the robotic arm gantry moves in a first direction and the robotic arm moves along the gantry in a second direction.

In another embodiment, the first and second directions are substantially perpendicular.

In some embodiments, the robotic arm includes a grip assembly that extends and retracts the robotic head from the robotic arm assembly.

In an embodiment, the extending and retracting is substantially perpendicular to the first and second directions.

In certain embodiments, the robotic head extends to acquire a slide rack assembly.

In some embodiments, the robotic head retracts to remove the slide rack assembly from a processing fluid bath or to leave the slide rack assembly in a processing fluid bath for an incubation.

In a particular embodiment, the robotic arm moves in a radial direction around a circular center.

In some embodiments, the continuous flow staining protocol comprises determining a slide rack assembly staining protocol for each slide rack assembly and calculating an order and an initiation time for each slide rack assembly staining protocol.

In a particular embodiment, the initiation time for each subsequent slide rack assembly staining protocols is at a time where it can proceed through its slide rack assembly staining protocol.

In another particular embodiment, the order of slide rack assembly staining protocol is the order in which the plurality of slide rack assembly staining protocols are completed in the shortest period of time.

In an embodiment, determining the timing and movement of the robotic arm between processing fluid baths comprises receiving input data regarding the plurality of processing fluids and the type of specimen on the microscope slides.

According to an embodiment, receiving input data comprises a user inputting data or a bar code reader scanning a bar code located on the plurality of slide rack assemblies.

According to another aspect of the disclosure, a method of performing an automated staining, the method comprising providing an automated stainer comprising: a plurality of slide rack assemblies with locations for multiple microscope slides; a plurality of processing fluid baths, each comprising a processing fluid; a robotic arm with a robotic head that releasably grasps the at least one slide rack assembly; and a processor that determines diming timing and movement of the robotic arm to move the plurality of slide rack assembly between the processing fluid baths. The method further comprising: receiving data regarding specimens on the microscope slides and the processing fluids; determining a continuous flow staining protocol that includes the timing and movement of the plurality of slide rack assemblies based on the specimens or the processing fluids; and moving the slide rack assemblies according to the continuous flow staining protocol via the robotic arm.

In an embodiment, the continuous flow staining protocol comprises determining a slide rack assembly staining protocol for each slide rack assembly and calculating an order and an initiation time for each slide rack assembly staining protocol.

In another embodiment, the initiation time for each subsequent slide rack assembly staining protocols is at a time where it can proceed through its slide rack assembly staining protocol.

In a particular embodiment, the order of slide rack assembly staining protocol is the order in which the plurality of slide rack assembly staining protocols are completed in the shortest period of time.

According to another aspect of the disclosure, a processor comprising a non-transitory computer readable medium having instructions stored thereon, the instructions being executable by one or more processors and the instructions configured to execute the method of claim 13.

The invention claimed is:

1. An automated stainer comprising:
    a plurality of slide rack assemblies with locations for multiple microscope slides;
    a plurality of processing fluid baths, each comprising a processing fluid;
    a robotic arm with a robotic head that releasably grasps the at least one slide rack assembly;
    a heating chamber with a locking lid that creates a pressurized internal chamber; and
    a processor that determines timing and movement of the robotic arm between the processing fluid baths by: (i) receiving input data regarding the plurality of processing fluids and the type of specimen on the microscope slides, and (ii) moving the slide rack assemblies based on the specimens, the processing fluids, or both the specimens and the processing fluids,
    wherein the robotic arm dispenses an antigen retrieval agent to an antigen retrieval rack in the heating chamber and water to the heating chamber.

2. The automated stainer of claim 1, wherein the processor comprises non-transitory computer readable medium storing a program to time and move the robotic arm based on the specimen, the plurality of processing fluids, or both the specimens and the processing fluids.

3. The automated stainer of claim 1, wherein at least one of:
    the processing fluids include at least one of: antigen retrieval agent, at least one detection reagent, a wash buffer, water, or a combination thereof;
    the processing fluids are used for multiple slide rack assemblies;
    the processing fluids are used for 50 to 70 microscope slides; or
    a combination thereof.

4. The automated stainer of claim 3, wherein the detection reagent is at least one of a primary antibody, a secondary antibody specific to the primary antibody with a conjugated enzyme, a substrate specific to the conjugated enzyme, a counterstain, or a combination thereof.

5. The automated stainer of claim 4, wherein the plurality of processing fluid baths includes at least one processing fluid selected from the primary antibody, the secondary antibody, or both, and the associated processing fluid bath or baths are configured to receive a slide rack assembly.

6. The automated stainer of claim 1, wherein the robotic arm locks and unlocks the locking lid.

7. The automated stainer of claim 1, wherein the robotic arm is mounted on a robotic arm gantry.

8. The automated stainer of claim 7, wherein at least one of:
    the robotic arm gantry and robotic arm facilitate movement three dimensionally; and
    the robotic arm gantry moves in a first direction and the robotic arm moves along the gantry in a second direction.

9. The automated stainer of claim 8, wherein at least one of:
    the first and second directions are substantially perpendicular;
    the robotic arm includes a grip assembly that extends and retracts the robotic head from the robotic arm assembly; or
    a combination thereof.

10. The automated stainer of claim 9, wherein at least one of:
    extending and retracting is substantially perpendicular to the first and second directions;
    the robotic head extends to acquire a slide rack assembly;
    the robotic head retracts to remove the slide rack assembly from a processing fluid bath or to leave the slide rack assembly in a processing fluid bath for an incubation; or
    a combination thereof.

11. The automated stainer of claim 1, wherein the robotic arm moves in a radial direction around a circular center.

12. The automated stainer of claim 1, wherein at least one:
    a initiation time for each subsequent slide rack assembly staining protocols is at a time where it can proceed through its slide rack assembly staining protocol;
    a order of slide rack assembly staining protocol is the order in which the plurality of slide rack assembly staining protocols are completed in the shortest period of time; or
    a combination thereof.

13. The automated stainer of claim 1, wherein receiving input data comprises a user inputting data or a bar code reader scanning a bar code located on the plurality of slide rack assemblies.

14. A method of performing an automated staining, the method comprising:
providing an automated stainer comprising:
a plurality of slide rack assemblies with locations for multiple microscope slides;
a plurality of processing fluid baths, each comprising a processing fluid;
a robotic arm with a robotic head that releasably grasps the at least one slide rack assembly;
a heating chamber with a locking lid, wherein the robotic arm dispenses an antigen retrieval agent to an antigen retrieval rack in the heating chamber and water to the heating chamber; and
a processor that determines timing and movement of the robotic arm to move the plurality of slide rack assembly between the processing fluid baths;
receiving data regarding specimens on the microscope slides and the processing fluids; and
moving the slide rack assemblies according based on the specimens, the processing fluids, or both the specimens and processing fluids, via the robotic arm.

15. The method of claim 14, wherein at least one of the following:
a initiation time for each subsequent slide rack assembly staining protocols is at a time where it can proceed through its slide rack assembly staining protocol;
a order of slide rack assembly staining protocol is the order in which the plurality of slide rack assembly staining protocols are completed in the shortest period of time; or
a combination thereof.

16. A processor comprising a non-transitory computer readable medium having instructions stored thereon, the instructions being executable by one or more processors and the instructions configured to execute a method to be performed on an automated stainer comprising: (1) a plurality of slide rack assemblies with locations for multiple microscope slides; a plurality of processing fluid baths, each comprising a processing fluid; (2) a robotic arm with a robotic head that releasably grasps the at least one slide rack assembly; (3) a heating chamber with a locking lid, wherein the robotic arm dispenses an antigen retrieval agent to an antigen retrieval rack in the heating chamber and water to the heating chamber; and (4) a processor that determines timing and movement of the robotic arm to move the plurality of slide rack assembly between the processing fluid baths, the method comprising receiving data regarding specimens on the microscope slides and the processing fluids; and moving the slide rack assemblies based on the specimens, the processing fluids, or both the specimens and processing fluids via the robotic arm.

17. The processor of claim 16, wherein the robotic arm locks and unlocks the locking lid.

18. The method of claim 14, wherein the robotic arm locks and unlocks the locking lid.

19. The method of claim 14, wherein the plurality of processing fluid baths includes at least one processing fluid selected from the primary antibody, the secondary antibody, or both, and the associated processing fluid bath or baths are configured to receive a slide rack assembly.

* * * * *